(12) United States Patent
Gardener et al.

(10) Patent No.: US 10,808,034 B2
(45) Date of Patent: Oct. 20, 2020

(54) ANTI-PRP ANTIBODIES AND USES THEREOF

(71) Applicant: MedImmune Limited, Cambridge (GB)

(72) Inventors: Matthew Gardener, Cambridge (GB); Jayne Hammersley, Cambridge (GB); Maria Groves, Cambridge (GB); Gareth Rees, Cambridge (GB); Sadhana Podichetty, Cambridge (GB); Andrew Billinton, Cambridge (GB)

(73) Assignee: MedImmune Limited, Cambridge (GB)

( * ) Notice: Subject to any disclaimer, the term of this patent is extended or adjusted under 35 U.S.C. 154(b) by 12 days.

(21) Appl. No.: 16/093,687

(22) PCT Filed: Apr. 4, 2017

(86) PCT No.: PCT/EP2017/058010
§ 371 (c)(1),
(2) Date: Oct. 15, 2018

(87) PCT Pub. No.: WO2017/178288
PCT Pub. Date: Oct. 19, 2017

(65) Prior Publication Data
US 2019/0062442 A1 Feb. 28, 2019

Related U.S. Application Data

(60) Provisional application No. 62/323,117, filed on Apr. 15, 2016.

(51) Int. Cl.
*C07K 16/18* (2006.01)
*C07K 16/28* (2006.01)

(52) U.S. Cl.
CPC ...... *C07K 16/2872* (2013.01); *C07K 2317/21* (2013.01); *C07K 2317/24* (2013.01); *C07K 2317/33* (2013.01); *C07K 2317/55* (2013.01); *C07K 2317/622* (2013.01); *C07K 2317/76* (2013.01); *C07K 2317/92* (2013.01)

(58) Field of Classification Search
CPC ................. C07K 16/2782; C07K 2317/56
See application file for complete search history.

(56) References Cited

U.S. PATENT DOCUMENTS

| | | | |
|---|---|---|---|
| 5,500,362 | A | 3/1996 | Robinson et al. |
| 5,821,337 | A | 10/1998 | Carter et al. |
| 9,217,036 | B2 | 12/2015 | Strittmatter et al. |
| 2003/0087407 | A1 | 5/2003 | Soto-Jara |
| 2005/0222036 | A1 | 10/2005 | During |
| 2015/0203591 | A1 | 7/2015 | Yancopoulos et al. |
| 2016/0176972 | A1 | 6/2016 | Strittmatter et al. |

FOREIGN PATENT DOCUMENTS

| | | |
|---|---|---|
| WO | WO-2005103081 A2 | 11/2005 |
| WO | WO-2007099346 A1 | 9/2007 |
| WO | WO-20080134034 A1 | 11/2008 |
| WO | WO-2009018625 A1 | 2/2009 |
| WO | WO-2011038575 A1 | 4/2011 |
| WO | WO-2017178288 A1 | 10/2017 |

OTHER PUBLICATIONS

Golabek, A., et al., "Amyloid beta binding proteins in vitro and in normal human cerebrospinal fluid," Neurosci Lett 191(1-2):79-82, Elsevier, Netherlands (1995).
Hampel, H., et al., "The future of Alzheimer's disease: The next 10 years," Progress in Neurobiology 95:718-728, Elsevier, Netherlands (2011).
Hirsch, T.Z., et al., "PrP$^c$ signaling in neurons: From basics to clinical challenges," Biochimie:1-10, Elsevier, Netherlands (2014).
Pankiewicz, J., et al., "Clearance and prevention of prion infection in cell cultures by anti-PrP antibodies," European Journal of Neuroscience 23:2653-2647, Federation of European Neuroscience Societies and Blackwell Publishing Ltd., Belgium (2006).
Perrin, R.J., et al., "Multimodal techniques for diagnosis and prognosis of Alzheimer's disease," Nature 461:916-922, Macmillan Publishers Limited United Kingdom (2009).
Vickers, J., "A Vaccine Against Alzheimer's Disease," Drugs Aging 19:488-494, Adis International Limited, New Zealand (2002).
Westergard, L., et al., "The Cellular Prior Protein (PrP$^c$): Its Physiological Function and Role in Disease," Biochim Biophys Act 1772(6):629-644, Elsevier, Netherlands (2007).
Zeisel, J., et al., "Non-pharmacological treatment for Alzheimer's disease: A mind-brain approach," American Journal of Alzheimer's Disease & Other Dementias 15(6):331-340, Sage Journals, United Sates (1999).
International Search Report and Written Opinion dated Sep. 19, 2008 in International Application No. PCT/US08/05427, International Searching Authority, United States, 8 pages.
Baumann, F., et al., "Lethal reparkcessive myelin toxicity of prion protein lacking its central domain," EMBO J. 26:538-547, Nature Publishing Group, United Kingdom (Jan. 2007).
Büeler, H., et al., "Normal development and behaviour of mice lacking the neuronal cell-surface PrP protein," Nature 356: 577-582, Nature Publishing Group, United Kingdom (1992).
Chapman, P., et al., "Impaired synaptic plasticity and learning in aged amyloid precursor protein transgenic mice," Nat. Neurosci. 2: 271-276, Nature Publishing Group, United States (1999).

(Continued)

*Primary Examiner* — Robert C Hayes
(74) *Attorney, Agent, or Firm* — White & Case LLP

(57) ABSTRACT

The present disclosure provides antibodies and antigen-binding fragments capable of binding PrP$^C$. The disclosure further provides methods for making and using the antibodies and antigen-binding fragments.

12 Claims, 3 Drawing Sheets
Specification includes a Sequence Listing.

(56) References Cited

OTHER PUBLICATIONS

Chen, G., et al., "A learning deficit related to age and β-amyloid plaques in a mouse model of Alzheimer's disease," *Nature* 408: 975-979, Nature Publishing Group, United Kingdom (2000).
Chromy, B., et al., "Self-Assembly of Aβ$_{1-42}$ into Globular Neurotoxins," *Biochemistry* 42:12749-12760, American Chemical Society, United States (2003).
Cleary, J., et al., "Natural oligomers of the amyloid-β protein specifically disrupt cognitive function," *Nat. Neurosci.* 8:79-84, Nature Publishing Group, United States (2005).
Haass, C. and Selkoe, D.J., "Soluble protein oligomers in neurodegeneration: lessons from the Alzheimer's amyloid β-peptide," *Nat. Rev. Mol. Cell Biol.* 8:101-112, Nature Publishing Group, United Kingdom (Feb. 2007).
Hardy, J. and Selkoe, D.J., "The Amyloid Hypothesis of Alzheimer's disease: Progress and Problems on the Road to Therapeutics," *Science* 297:353-356, American Association for the Advancement of Science, United States (2002).
Jankowsky, J., et al., "Mutant presenilins specifically elevate the levels of the 42 residue β-amyloid peptide in vivo: evidence for augmenation of a 42-specific γ secretase," *Hum. Mol. Genet.* 13:159-170, IRL Press at Oxford University Press, United Kingdom (2004).
Knobloch, M., et al., "Aβ Oligomer-Mediated Long-Term Potentiation Impairment Involves Protein Phosphatase 1-Dependent Mechanisms," *J. Neurosci.* 27:7648-7653, Society for Neuroscience, United States (Jul. 2007).
Lacor, P., et al., "Aβ Oligomer-Induced Aberrations in Synapse Composition, Shape, and Density Provide a Molecular Basis for Loss of Connectivity in Alzheimer's disease," *J. Neurosci.* 27:796-807, Society for Neuroscience, United States (Jan. 2007).
Lacor, P., et al., "Synaptic Targeting by Alzheimer's-Related Amyloid β Oligomers," *J. Neurosci.* 24:10191-10200, Society for Neuroscience, United States (2004).
Lesné, S., et al., "A specific amyloid-β protein assembly in the brain impairs memory," *Nature* 440:352-357, Nature Publishing Group, United Kingdom (Mar. 2006).
Li, A., et al., "Neonatal lethality in transgenic mice expressing prion protein with a deletion of residues 105-125," *EMBO J.* 26:548-558, Nature Publishing Group, United Kingdom (Jan. 2007).
Lledo, P.-M., et al., "Mice deficient for prion protein exhibit normal neuronal excitability and synaptic transmission in the hippocampus," *Proc. Natl. Acad. Sci. U.S.A.* 93:2403-2407, National Academy of Sciences, United States (1996).
Manson, J., et al., "129/Ola Mice Carrying a Null Mutation in PrP that abolishes mRNA Production Are Developmentally Normal," *Mol. Neurobiol.* 8:121-127, Humana Press, United States (1994).
Prusiner, S., "Prions," *Proc. Natl. Acad. Sci. U.S.A.* 95:13363-13383, National Academy of Sciences, United States (1998).
Rajagopalan, S., et al., "Neogenin mediates the action of repulsive guidance molecule," *Nat. Cell Biol.* 6: 756-762, Macmillan Magazines Ltd., United Kingdom (2004).
Riek, R., et al., NMR structure of the mouse prion protein domain PrP(121-231), *Nature* 382:180-82, Nature Publishing Group, United Kingdom (1996).
Shankar, G., et al., "Natural Oligomers of the Alzheimer Amyloid-β Protein Induce Reversible Synapse Loss by Modulating an NMDA-Type Glutamate Receptor-Dependent Signaling Pathway," *J. Neurosci.* 27:2866-2875, Society for Neuroscience, United States (Mar. 2007).
Solforosi, L., et al., "Cross-Linking Cellular Prion Protein Triggers Neuronal Apoptosis in Vivo," *Science* 303: 1514-1516, American Association for the Advancement of Science, United States (2004).
Viles, J., et al., "Copper binding to the prion protein: Structural implications of four identical cooperative binding sites," *Proc. Natl. Acad. U.S.A.* 96:2042-47, National Academy of Sciences, United States (1999).
Walsh, D., et al., "Naturally secreted oligomers of amyloid β protein potently inhibit hippocampal long-term potentiation in vivo," *Nature* 416:535-539, Nature Publishing Group, United Kingdom (2002).

Dermaut, B., et al., "PRNP Val129 Homozygosity Increases Risk for Early Onset Alzheimer's Disease," *Ann. Neurol.* 53:409-12, Wiley-Liss, Inc., United States(2003).
Filesi, I., et al., "Selective re-routing of prion protein to proteasomes and alteration of its vesicular secretion prevent PrP$^{Sc}$ formation," *J. Neurochemistry* 101:1516-26, Int'l Society for Neurochemistry, United Kingdom (2007).
McNeill, A., "A Molecular Analysis of Prion Protein Expression in Alzheimer's Disease," *McGill J. Medicine* 8:7-14, MJM, Canada (2004).
Schwarze-Eicker, K., et al., "Prion protein (PrP$^c$) promotes B-amyloid plaque formation," *Neurobiology of Aging* 26:1177-82, Elsevier Inc., United States (2005).
Parkin, E.T., et al., "Cellular prion protein regulates β-secretase cleavage of the Alzheimer's amyloid precursor protein," *PNAS* 104(26)11062-11067, The National Academy of Sciences of the USA, United States (2007).
Yehiely, F., et al., "Identification of Candidate Proteins Binding to Prion Protein," *Neurobiology of Disease* 3:339-355, Academic Press, United States (1997).
Stuke, A.W., and Strom, A., "Tetracycline-regulated highly inducible expression of the human prion protein in murine 3t3 cells," *Protein Expression and Purification* 39:8-17, Elsevier Inc., United States (2005).
Adams, J.M., et al., "The C-myc Oncogene Driven by Immunoglobulin Enhancers Induces Lymphoid Malignancy in Transgenic Mice," *Nature* 318(6046):533-538, Nature Publishing Group, England (Dec. 1985).
Alexander, W.S., et al., "Expression of the C-myc Oncogene Under Control of an Immunoglobulin Enhancer in Eμ-myc Transgenic Mice," *Molecular and Cellular Biology* 7(4):1436-1444, American Society for Microbiology, United States (Apr. 1987).
Altschul, S.F., et al., "Basic Local Alignment Search Tool," *Journal of Molecular Biology* 215(3):403-410, Elsevier, England (Oct. 1990).
Altschul, S.F., et al., "Gapped BLAST and PSI-BLAST: A New Generation of Protein Database Search Programs," *Nucleic Acids Research* 25(17):3389-3402, Oxford University Press, England (Sep. 1997).
Angal, S., et al., "A Single Amino Acid Substitution Abolishes the Heterogeneity of Chimeric Mouse/Human (IgG4) Antibody," *Molecular Immunology* 30(1):105-108, Pergamon Press, England (Jan. 1993).
Bernoist and Chambon, "In Vivo Sequence Requirements of the Sv40 Early Promoter Region," *Nature* 290(5804):304-310, Nature Publishing Group, England (Mar. 1981).
Brinster, R.L., et al., "Regulation of Metallothionein-thymidine Kinase Fusion Plasmids Injected Into Mouse Eggs," *Nature* 296(5852):39-42, Nature Publishing Group, England (Mar. 1982).
Brodeur, B.R., et al., "Mouse-Human Myeloma Partners for the Production of Heterohybridomas," in *Monoclonal Antibody Production Techniques and Applications* :pp. 51-63, Marcel Dekker, Inc., United States (1987).
Brown, M., et al., "Tolerance to Single, but not Multiple, Amino Acid Replacements in Antibody VH CDR2: A Means of Minimizing B Cell Wastage from Somatic Hypermutation?," *Journal of Immunology* 156(9):3285-3291, American Association of Immunologists, United States (May 1996).
Brundin, P., et al, "Prion-like Transmission of Protein Aggregates in Neurodegenerative Diseases," *Nature Reviews. Molecular Cell Biology* 11(4):301-307, Nature Publications Group, England (Apr. 2010).
Checkoway, H., et al, "Neurodegenerative Diseases," *IARC Scientific Publications* 163:407-419, International Agency for Research on Cancer, France (2011).
Chung, E., et al, "Anti-PRPC Monoclonal Antibody Infusion as a Novel Treatment for Cognitive Deficits in an Alzheimer's Disease Model Mouse," *BMC Neuroscience* 11:130, Biomed Central, England (Oct. 2010).
Clynes, R., et al., "Fc Receptors Are Required in Passive and Active Immunity to Melanoma," *Proceedings of the National Academy of Sciences of the USA* 95(2):652-656, National Academy of Sciences, United States (1998).

(56) References Cited

OTHER PUBLICATIONS

Daramola, O., et al., "A High-yielding Cho Transient System: Coexpression of Genes Encoding Ebna-1 and Gs Enhances Transient Protein Expression," Biotechnology Progress 30(1):132-141, American Institute of Chemical Engineers, United States (Jan.-Feb. 2014).

De Boer, H.A., et al., "The Tac Promoter: a Functional Hybrid Derived From the Trp and Lac Promoters," Proceedings of the National Academy of Sciences of the United States of America 80(1):21-25, National Academy of Sciences, United States (Jan. 1983).

Douthwaite, J.A., et al., "Affinity Maturation of a Novel Antagonistic Human Monoclonal Antibody With a Long Vh Cdr3 Targeting the Class a Gpcr Formyl-peptide Receptor 1," MAbs, 7(1):152-166, Landes Bioscience, United States (2015).

Ehring, "Hydrogen Exchange/Electrospray Ionization Mass Spectrometry Studies of Structural Features of Proteins and Protein/Protein Interactions," Analytical Biochemistry 267 (2):252-259,Elsevier, Netherlands (1999).

Engen, J.R. and Smith, D.L., "Investigating Protein Structure and Dynamics by Hydrogen Exchange MS," Analytical Chemistry 73(9):256A-265A, American Chemical Society, United States (May 2001).

Freir, D.B., et al, "Interaction Between Prion Protein and Toxic Amyloid Beta Assemblies Can Be Therapeutically Targeted at Multiple Sites," Nature Communications 2:336, (Jun. 2011).

Frost, B and Diamond, M.I, "Prion-like Mechanisms in Neurodegenerative Diseases," Nature Reviews. Neuroscience 11(3):155-159, Nature Publication Group, England (Mar. 2010).

Gonnet, G.H., et al., "Exhaustive Matching of the Entire Protein Sequence Database," Science 256(5062):1443-1445, American Association for the Advancement of Science, United States (1992).

Grosschedl, R., et al., "Introduction of a Mu Immunoglobulin Gene Into the Mouse Germ Line: Specific Expression in Lymphoid Cells and Synthesis of Functional Antibody," Cell 38(3):647-658, Cell Press, United States (Oct. 1984).

Haas, L.T., et al, "Therapeutic Molecules and Endogenous Ligands Regulate the Interaction Between Brain Cellular Prion Protein (Prpc) and Metabotropic Glutamate Receptor 5 (MGLURS)," The Journal of Biological Chemistry 289(41):28460-28477, American Society for Biochemistry and Molecular Biology, United States (Oct. 2014).

Hammer, R.E., et al., "Diversity of Alpha-fetoprotein Gene Expression in Mice Is Generated by a Combination of Separate Enhancer Elements," Science 235(4784):53-58, American Association for the Advancement of Science, United States (Jan. 1987).

Hanahan, D, "Heritable Formation of Pancreatic Beta-cell Tumours in Transgenic Mice Expressing Recombinant Insulin/simian Virus 40 Oncogenes," Nature 315(6015):115-122, Nature Publishing Group, England (May 1985).

Hawkins, R.E., et al., "Selection of phage antibodies by binding affinity. Mimicking affinity maturation," Journal of Molecular Biology 226(3):889-896, Elsevier Science, United States (Aug. 1992).

Hochleitner, E.O., et al. , "Characterization of a Discontinuous Epitope of the Human Immunodeficiency Virus (Hiv) Core Protein P24 by Epitope Excision and Differential Chemical Modification Followed by Mass Spectrometric Peptide Mapping Analysis," Protein Science 9(3):487-496, Cold Spring Harbor Laboratory Press, United States (Mar. 2000).

Jones, D.R., et al, "A Camelid Anti-prp Antibody Abrogates Prp$^{Sc}$ Replication in Prion-permissive Neuroblastoma Cell Lines," Plos One 5(3):e9804, Public Library of Science, United States (Mar. 2010).

Junghans, R.P., et al., "Anti-tac-h, a Humanized Antibody to the Interleukin 2 Receptor With New Features for Immunotherapy in Malignant and Immune Disorders," Cancer Research 50(5):1495-1502, American Association for Cancer Research, United States (Mar. 1990).

Kelsey, G.D., et al., "Species- and Tissue-specific Expression of Human Alpha 1-antitrypsin in Transgenic Mice," Genes & Development 1(2):161-171, Cold Spring Harbor Laboratory Press, United States (Apr. 1987).

Klein, C., et al., "Progress in Overcoming the Chain Association Issue in Bispecific Heterodimeric IgG Antibodies," MAbs 4(6):653-663, Taylor & Francis, United States (Nov.-Dec. 2012).

Kohler, G. and Milstein, C., "Continuous Cultures of Fused Cells Secreting Antibody of Predefined Specificity," Nature 256(5517):495-497, Macmillan Journals Ltd., England (Aug. 1975).

Kollias, G., et al., "Regulated Expression of Human $^A$Gamma-, Beta-, and Hybrid Gamma Beta-globin Genes in Transgenic Mice: Manipulation of the Developmental Expression Patterns," Cell 46(1):89-94, Cell Press, United States (Jul. 1986).

Kozbor, D., et al., "A Human Hybrid Myeloma for Production of Human Monoclonal Antibodies," Journal of Immunology 133(6):3001-3005, American Association of Immunologists, United States (Dec. 1984).

Krumlauf, R., et al., "Developmental Regulation of Alpha-fetoprotein Genes in Transgenic Mice," Molecular and Cellular Biology 5(7):1639-1648, American Society for Microbiology, United States (Jul. 1985).

Kufer, P., et al., "A Revival of Bispecific Antibodies," Trends in Biotechnology 22(5):238-244, Elsevier Science Publishers, England (May 2004).

Langer, R., "New Methods of Drug Delivery," Science 249(4976):1527-1533, American Association for the Advancement of Science, United States (Sep. 1990).

Lauren, J., et al., "Cellular Prion Protein Mediates Impairment of Synaptic Plasticity by Amyloid-beta Oligomers," Nature 457(7233):1128-1132, Nature Publishing Group, England (Feb. 2009).

Leder, A., et al., "Consequences of Widespread Deregulation of the C-myc Gene in Transgenic Mice: Multiple Neoplasms and Normal Development," Cell 45(4):485-495, Cell Press, United States (May 1986).

Linden, R., et al, "Physiology of the Prion Protein," Physiological Reviews 88(2):673-728, American Physiological Society, United States (Apr. 2008).

Lloyd, C., et al., "Modelling the Human Immune Response: Performance of a $10^{11}$ Human Antibody Repertoire Against a Broad Panel of Therapeutically Relevant Antigens," Protein Engineering, Design and Selection, 22(3):159-168, Oxford University Press, England (Mar. 2009).

MacDonald, "Expression of the Pancreatic Elastase I Gene in Transgenic Mice," Hepatology 7:425-515, (1987).

Magram, J., et al., "Developmental Regulation of a Cloned Adult Beta-globin Gene in Transgenic Mice," Nature 315(6017):338-340, Nature Publishing Group, England (May 1985).

Mason, A.J., et al., "The Hypogonadal Mouse: Reproductive Functions Restored by Gene Therapy," Science 234(4782):1372-1378, American Association for the Advancement of Science, United States (Dec. 1986).

Mordenti, J., et al., "Interspecies Scaling of Clearance and volume of Distribution Data for Five Therapeutic Proteins," Pharmaceutical Research 8(11):1351-1359, Kluwer Academic/Plenum Publishers, United States (Nov. 1991).

Oganesyan, V., et al., "Structural Characterization of a Human Fc Fragment Engineered for Lack of Effector Functions," Acta Crystallographica. Section D, Biological Crystallography 64(Pt 6):700-704, Wiley-Blackwell, United States (Jun. 2008).

Ohsawa, N., et al, "Therapeutic Effect of Peripheral Administration of an Anti-prion Protein Antibody on Mice Infected With Prions," Microbiology and Immunology 57(4):288-297, Wiley-Blackwell, Australia (Apr. 2013).

Ornitz, D.M., et al., "Elastase I Promoter Directs Expression of Human Growth Hormone and Sv40 T Antigen Genes to Pancreatic Acinar Cells in Transgenic Mice," Cold Spring Harbor Symposia on Quantitative Biology 50:399-409, Cold Spring Harbor Laboratory Press, United States (1985).

Panegyres, P.K and Armari, E, "Therapies for Human Prion Diseases," American Journal of Neurodegenerative Disease 2(3):176-186, E-century Publishing Corporation, United States (Sep. 2013).

(56) References Cited

OTHER PUBLICATIONS

Pearson, W.R., "Using the FASTA Program to Search Protein and DNA Sequence Databases," Methods in Molecular Biology 24:307-331, Humana Press, United States (Feb. 1994).

Pinkert, C.A., et al., "An Albumin Enhancer Located 10 Kb Upstream Functions Along With Its Promoter to Direct Efficient, Liver-specific Expression in Transgenic Mice," Genes & Development 1(3):268-276, Cold Spring Harbor Laboratory Press, United States (May 1987).

Powell, M.F., et al., "Compendium of Excipients for Parenteral Formulations," PDA Journal of Pharmaceutical Science and Technology / PDA 52(5):238-311, PDA (Parenteral Drug Association), United States (Sep. 1998).

Prusiner, S.B, "Scrapie Prions," Annual Review of Microbiology 43:345-374, Annual Reviews, United States (1989).

Prusiner, S.B, "Prion Diseases and the BSE Crisis," Science 278(5336):245-251, American Association for the Advancement of Science, United States (Oct. 1997).

Readhead, C., et al., "Expression of a Myelin Basic Protein Gene in Transgenic Shiverer Mice: Correction of the Dysmyelinating Phenotype," Cell 48(4):703-712, Cell Press, United States (Feb. 1987).

Reineke, U, "Antibody Epitope Mapping Using Arrays of Synthetic Peptides," Methods Molecular Biology 248:443-463, Humana Press, United States (2004).

Sefton, M.V., "Implantable Pumps," Critical Reviews in Biomedical Engineering 14(3):201-240, Begell House, United States (1987).

Shani, M, "Tissue-specific Expression of Rat Myosin Light-chain 2 Gene in Transgenic Mice," Nature 314(6008):283-286, Nature Publishing Group, England (Mar. 1985).

Shimizu, Y., et al, "A Novel Anti-prion Protein Monoclonal Antibody and Its Single-chain Fragment Variable Derivative With Ability to Inhibit Abnormal Prion Protein Accumulation in Cultured Cells," Microbial Immunology 54(2):112-121, Wiley-Blackwell, Australia (Feb. 2010).

Kim, C.H., et al., "Synthesis of Bispecific Antibodies using Genetically Encoded Unnatural Amino Acids," Journal of the American Chemistry Society 134(24):9918-9921, American Chemistry Society, United States (Jun. 2012).

Kwon, D., "The Great Brain Drain [now titled, Are Prions behind All Neurodegenerative Diseases]," Journal Scientific American 313(5):17-18, Nature Publishing Group, United States (Nov. 2015).

Swift, G.H., et al., "Tissue-specific Expression of the Rat Pancreatic Elastase I Gene in Transgenic Mice," Cell 38(3):639-646, Cell Press, United States (Oct. 1984).

Taylor, L.D., et al., "A Transgenic Mouse That Expresses a Diversity of Human Sequence Heavy and Light Chain Immunoglobulins," Nucleic Acids Research 20(23):6287-6295, Oxford University Press, England (1992).

Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).

Vaughan, T.J., et al., "Human Antibodies with Sub-nanomolar Affinities Isolated from a Large non-Immunized Phage Display Library," Nature Biotechnology 14(3):309-314, Nature Publishing Co., United States (Mar. 1996).

Villa-Komaroff, L., et al., "A Bacterial Clone Synthesizing Proinsulin," Proceedings of the National Academy of Sciences of the United States of America 75(8):3727-3731, National Academy of Sciences, United States (Aug. 1978).

Wagner, M.J., et al, "Nucleotide Sequence of the Thymidine Kinase Gene of Herpes Simplex Virus Type 1," Proceedings of the National Academy of Sciences of the United States of America 78(3):1444-1445, National Academy of Sciences, United States (Mar. 1981).

White, A.R., et al, "Monoclonal Antibodies Inhibit Prion Replication and Delay the Development of Prion Disease," Nature 422(6927):80-83, Nature Publishing Group, England (Mar. 2003).

Wimo, A. and Prince, M., "World Alzheimer report 2010: The global economic impact of dementia ," Alzheimer's Disease International (ADI) 1-56, United Kingdom (Sep. 2010).

Wu ,G.Y and Wu ,C.H., "Receptor-mediated in Vitro Gene Transformation by a Soluble DNA Carrier System," The Journal of Biological Chemistry 262(10):4429-4432, American Society for Biochemistry and Molecular Biology, United States (Apr. 1987).

Yamamoto, T., et al., "Identification of a Functional Promoter in the Long Terminal Repeat of Rous Sarcoma Virus," Cell 22(3):787-797, Cell Press, United States (Dec. 1980).

Yamasaki, T., et al, "Comparison of the Anti-prion Mechanism of Four Different Anti-prion Compounds, Anti-prp Monoclonal Antibody 44b1, Pentosan Polysulfate, Chlorpromazine, and U18666a, in Prion-infected Mouse Neuroblastoma Cells ," Plos One 9(9):e106516, Public Library of Science, United States (Sep. 2014).

Zhou, J and Liu, B, "Alzheimer's Disease and Prion Protein ," Intractable and Rare Diseases Research 2(2):35-44, International Advancement Center for Medicine and Health Research Corporation, Japan (May 2013).

International Search Report and Written Opinion dated Jul. 17, 2017 in International Application No. PCT/EP2017/058010, European Patent Office, Iceland, 12 pages.

International Preliminary Report on Patentability dated Oct. 16, 2018 in International Application No. PCT/EP2017/058010, International Bureau of WIPO, Switzerland, 8 pages.

ANTI-PRP ANTIBODIES AND USES THEREOF

CROSS-REFERENCE TO RELATED APPLICATIONS

This application claims the benefit of priority from U.S. Provisional Application No. 62/323,117, filed Apr. 15, 2016. The specification of the foregoing application is incorporated herein by reference in its entirety.

BACKGROUND OF THE DISCLOSURE

Degenerative diseases of the nervous system impose a significant worldwide medical and public health burden. The prevalence and incidence of these diseases rise dramatically with age and the number of cases is expected to increase with extended life expectancy in many countries (Checkoway H et al. IARC Sci Publ. 2011; (163):407-19). Alzheimer's Disease International (ADI) estimated in 2010 that there were 35.6 million people with Alzheimer's Disease worldwide, and that this number will grow to 115.4 million people by 2050 (Wimo A and Prince M. ADI Report. 2010 Sep. 21; 1-56). An estimated 5.3 million Americans of all ages have Alzheimer's disease in 2015, of which 5.1 million people are age 65 and older. By 2050, the number of people age 65 and older with Alzheimer's disease in the U.S. may nearly triple, from 5.1 million to a projected 13.8 million, in the absence of medical intervention to prevent or cure the disease.

Prions are transmissible particles that are devoid of nucleic acid and seem to be composed exclusively of a modified protein ($PrP^{Sc}$). The normal, cellular prion protein ($PrP^c$) is encoded by a cellular gene (Prnp) and, in its mature form, is about 210 amino acid residues with a molecular weight of 33-35 kD. It is converted into $PrP^{Sc}$ through a posttranslational process during which it acquires a high β-sheet content (Prusiner S B. Science. 1997 Oct. 10; 278(5336):245-51). It is believed that accumulation of $PrP^{Sc}$ is the main pathogenic event leading to neurodegeneration (Linden R et al. Physiological Reviews. 2008 Apr. 1; 88(2): 673-728). Prions cause a number of fatal disorders in different mammalian species. These diseases are characterized by a spongiform neurodegeneration of the brain and the amyloid fibrils deposition composed by the abnormal, misfolded form of the cellular prion protein. These include diseases such as Iatrogenic Creutzfeldt-Jakob Disease (CJD) in humans, Variant Creutzfeldt-Jakob Disease (vCJD), Familial CJD, Sporadic CJD, Gerstmann-Straussler-Scheinker Syndrome, Fatal Familial Insomnia, Kuru, Alpers Syndrome (progressive sclerosing poliodystrophy), Bovine Spongiform Encephalopathy (BSE) in cattle, Chronic Wasting Disease (CWD) in cervids, Scrapie in sheep, Transmissible mink encephalopathy, Feline spongiform encephalopathy and Ungulate spongiform encephalopathy. The human prion diseases can present as sporadic, genetic, or infectious disorders (Prusiner S B. Annu. Rev. Microbiol. 1989; (43): 345).

Neurodegenerative diseases are commonly associated with the accumulation of intracellular or extracellular protein aggregates, such as α-synuclein in Parkinson's disease, β-amyloid and tau in Alzheimer's disease, huntingtin in Huntington's disease and prion protein (PrP) in transmissible prion encephalopathies (Brundin P et al. Nat Rev Mol Cell Biol. 2010 April; 11(4): 301-307). A new understanding is emerging about neurodegenerative disorders such as Alzheimer's Disease, Parkinson's Disease, Huntington's Disease, amyotrophic lateral sclerosis (ALS), motor neuron diseases, tauopathies, etc that involve protein misfolding. Evidence suggests that protein-misfolding and subsequent propagation of these rogue proteins is a generic phenomenon shared with diseases caused by tau, α-synucleins and β-amyloid proteins (Panegyres P K and Armari E. Am J Neurodegener Dis. 2013; 2(3): 176-186). Further, there is mounting evidence to suggest that prion-like proteins may underlie the pathogenesis of these diseases and present a valuable target to develop novel therapies aimed at lowering prion protein levels, inhibiting its interaction with other proteins, and inhibiting prion formation (Kwon, D. Scientific American. 2015 Nov. 1). $PrP^c$ has been identified as a major player in mediating the toxicity of Aβ oligomers that leads to synaptic loss and cognitive impairment in Alzheimer's Disease. Therefore, targeting $PrP^c$, its interaction with Aβ oligomers, or downstream mediators can be considered the new line of choice for therapeutic development for treatment of Alzheimer's Disease (Jiayi Zhou J and Liu B. Intractable Rare Dis Res. 2013 May; 2(2): 35-44). New therapeutic strategies that block propagation of protein misfolding throughout the brain can halt neurodegenerative disease progression (Frost B and Diamond M I. Nat Rev Neurosci. 2010 March; 11(3): 155-159). A number of groups have shown in animal models that antibodies that efficiently bind to $PrP^c$ and that appear to block the binding site(s) of Aβ oligomers can have therapeutic effect on Alzheimer's Disease by preventing the Aβ oligomer/$PrP^c$-initiated noxious signaling (Jiayi Zhou J and Liu B. Intractable Rare Dis Res. 2013 May; 2(2): 35-44; and; Darragh B. Freir D B et al. Nat Commun. 2011 June; 2: 336; and; Chung E et al. BMC Neurosci. 2010; 11: 130)

There is currently no cure for Alzheimer's Disease. As of 2015, there are only five approved medications in the US for treating Alzheimer's Disease. These medications temporarily slow the worsening of symptoms and improve quality of life for those with Alzheimer's and their caregivers. As such, there is a need for new therapeutics for treating Alzheimer's Disease and other neurodegenerative disorders.

BRIEF SUMMARY OF THE DISCLOSURE

The present disclosure provides antibodies that bind human prion protein ("$PrP^C$"). The antibodies of the disclosure are useful, inter alia, for inhibiting $PrP^C$-mediated signaling and for treating diseases and disorders caused by or related to $PrP^C$ activity and/or signaling.

In some embodiments, the disclosure provides for an antibody or antigen-binding fragment, wherein the antibody or antigen-binding fragment comprises a light chain variable (VL) domain and a heavy chain variable (VH) domain; wherein the VH domain comprises CDR1, CDR2 and CDR3 of the amino acid sequence set forth in SEQ ID NO: 4. In some embodiments, the disclosure provides for an antibody or antigen-binding fragment, wherein the antibody or antigen-binding fragment comprises a light chain variable (VL) domain and a heavy chain variable (VH) domain; wherein the VL domain comprises CDR1, CDR2 and CDR3 of the amino acid sequence set forth in SEQ ID NO: 13. In some embodiments, the VH domain comprises: a VH CDR1 having the amino acid sequence of SEQ ID NO: 5; a VH CDR2 having the amino acid sequence of SEQ ID NO: 6; and a VH CDR3 having the amino acid sequence of SEQ ID NO: 7. In some embodiments, the VL domain comprises: a VL CDR1 having the amino acid sequence of SEQ ID NO: 14; a VL CDR2 having the amino acid sequence of SEQ ID NO: 15; and a VL CDR3 having the amino acid sequence of SEQ ID NO: 16. In some embodiments, the VH domain comprises framework regions that are at least 90% identical to the amino acid sequences of SEQ ID NO: 8, SEQ ID NO: 9, SEQ ID NO: 10 and SEQ ID NO: 11. In some embodiments, the VH domain comprises framework regions having the amino acid sequences of SEQ ID NO: 8, SEQ ID NO: 9, SEQ ID NO: 10 and SEQ ID NO: 11. In some embodiments, the VL domain comprises framework regions that are at least 90% identical to the amino acid sequences of SEQ ID NO: 17, SEQ ID NO: 18, SEQ ID NO: 19 and SEQ ID NO: 20. In some embodiments, the VL domain comprises framework regions having the amino acid sequences of SEQ ID NO: 17, SEQ ID NO: 18, SEQ ID NO: 19 and SEQ ID NO: 20. In some embodiments, the VH domain comprises an amino acid sequence that is at least 90% identical to SEQ ID NO: 4. In some embodiments, the VL domain comprises an amino acid sequence that is at least 90% identical to SEQ ID NO: 13. In some embodiments, the VH domain comprises an amino acid sequence that is at least 95% identical to SEQ ID NO: 4. In some embodiments, the VL domain comprises an amino acid sequence that is at least 95% identical to SEQ ID NO: 13. In some embodiments, the VH domain comprises the amino acid sequence of SEQ ID NO: 4. In some embodiments, the VL domain comprises the amino acid sequence of SEQ ID NO: 13. In some embodiments, the antibody or antigen-binding fragment is an antigen-binding fragment. In some embodiments, the antigen-binding fragment is an scFv. In some embodiments, the antigen-binding fragment is a Fab'. In some embodiments, the antibody or antigen-binding fragment is an antibody. In some embodiments, the antibody is a monoclonal antibody. In some embodiments, the antibody is an IgG antibody. In some embodiments, the antibody or antigen-binding fragment is humanized. In some embodiments, the antibody or antigen-binding fragment is human. In some embodiments, the antibody or antigen-binding fragment is encoded by a nucleic acid comprising a nucleotide sequence that is at least 90% identity to SEQ ID NO: 3. In some embodiments, the antibody or antigen-binding fragment is encoded by a nucleic acid comprising a nucleotide sequence that is at least 95% identity to SEQ ID NO: 3. In some embodiments, the antibody or antigen-binding fragment is encoded by a nucleic acid comprising the nucleotide sequence of SEQ ID NO: 3. In some embodiments, the antibody or antigen-binding fragment is encoded by a nucleic acid comprising a nucleotide sequence that is at least 90% identity to SEQ ID NO: 12. In some embodiments, the antibody or antigen-binding fragment is encoded by a nucleic acid comprising a nucleotide sequence that is at least 95% identity to SEQ ID NO: 12. In some embodiments, the antibody or antigen-binding fragment is encoded by a nucleic acid comprising the nucleotide sequence of SEQ ID NO: 12. In some embodiments, the antibody or antigen-binding fragment competes with 6D11 antibody for binding to $PrP^C$. In some embodiments, the antibody or antigen-binding fragment binds to human, rat, mouse and cynomolgus monkey $PrP^C$. In some embodiments, the antibody or antigen-binding fragment binds to human, rat, mouse and/or cynomolgus monkey $PrP^C$ with a $K_D$ of less than 1 nM. In some embodiments, the antibody or antigen-binding fragment binds to human, rat, mouse and/or cynomolgus monkey $PrP^C$ with a $K_D$ of less than 500 pM. In some embodiments, the antibody or antigen-binding fragment binds to human, rat, mouse and/or cynomolgus monkey $PrP^C$ with a $K_D$ of less than 100 pM. In some embodiments, the antibody or antigen-binding fragment binds to human, rat, mouse and/or cynomolgus monkey $PrP^C$ with a $K_D$ of less than 50 pM. In some embodiments, the antibody or antigen-binding fragment binds to human, rat, mouse and/or cynomolgus monkey $PrP^C$ with a $K_D$ of less than 25 pM.

In some embodiments, the disclosure provides for a nucleic acid capable of expressing any of the antibodies of antigen-binding fragments disclosed herein. In some embodiments, the disclosure provides for a nucleic acid comprising a nucleotide sequence that is at least 90% identical to SEQ ID NO: 3. In some embodiments, the disclosure provides for a nucleic acid comprising a nucleotide sequence that is at least 95% identical to SEQ ID NO: 3. In some embodiments, the disclosure provides for a nucleic acid comprising the nucleotide sequence of SEQ ID NO: 3. In some embodiments, the disclosure provides for a nucleic acid comprising a nucleotide sequence that is at least 90% identical to SEQ ID NO: 12. In some embodiments, the disclosure provides for a nucleic acid comprising a nucleotide sequence that is at least 95% identical to SEQ ID NO: 12. In some embodiments, the disclosure provides for a nucleic acid comprising the nucleotide sequence of SEQ ID NO: 12.

In some embodiments, the disclosure provides for a vector comprising any of the nucleic acids disclosed herein. In some embodiments, the disclosure provides for a host cell comprising any of the vectors disclosed herein.

In some embodiments, the disclosure provides for a composition comprising a pharmaceutically acceptable carrier and the antibodies or antigen-binding fragments disclosed herein.

In some embodiments, the disclosure provides for a method for treating a subject having a neurodegenerative disorder, comprising administering to the subject a pharmaceutically effective amount of the antibodies or antigen-binding fragments disclosed herein. In some embodiments, the disclosure provides for a method for treating a subject having a neurodegenerative disorder, comprising administering to the subject a pharmaceutically effective amount of any of the compositions disclosed herein. In some embodiments, the neurodegenerative disorder is Alzheimer's Disease. In some embodiments, the neurodegenerative disorder is a disease associated with misfolded PrP. In some embodiments, the neurodegenerative disorder is selected from the group consisting of: Creutzfeldt-Jakob Disease, Gerstmann-Sträussler-Schenker Disease or Fatal Familial Insomnia. In some embodiments, the subject is a human. In some embodiments, the subject is a non-human animal. In some embodiments, the neurodegenerative disorder is selected from the group consisting of bovine spongiform encephalopathy, scrapie, chronic wasting disease, transmissible mink encephalopathy, and spongiform encephalopathy.

In some embodiments, the disclosure provides for a method of producing any of the antibodies or antigen-binding fragments disclosed herein, comprising the steps of: expressing any of the nucleic acids disclosed herein in a cultured cell, and purifying the antibody or antigen-binding fragment.

BRIEF DESCRIPTION OF THE DRAWINGS

This patent or patent application filed contains at least one drawing executed in color. Copies of this patent or patent application publication with color drawing(s) will be provided by the Office upon request and payment of the necessary fee.

DETAILED DESCRIPTION

Figure 1:
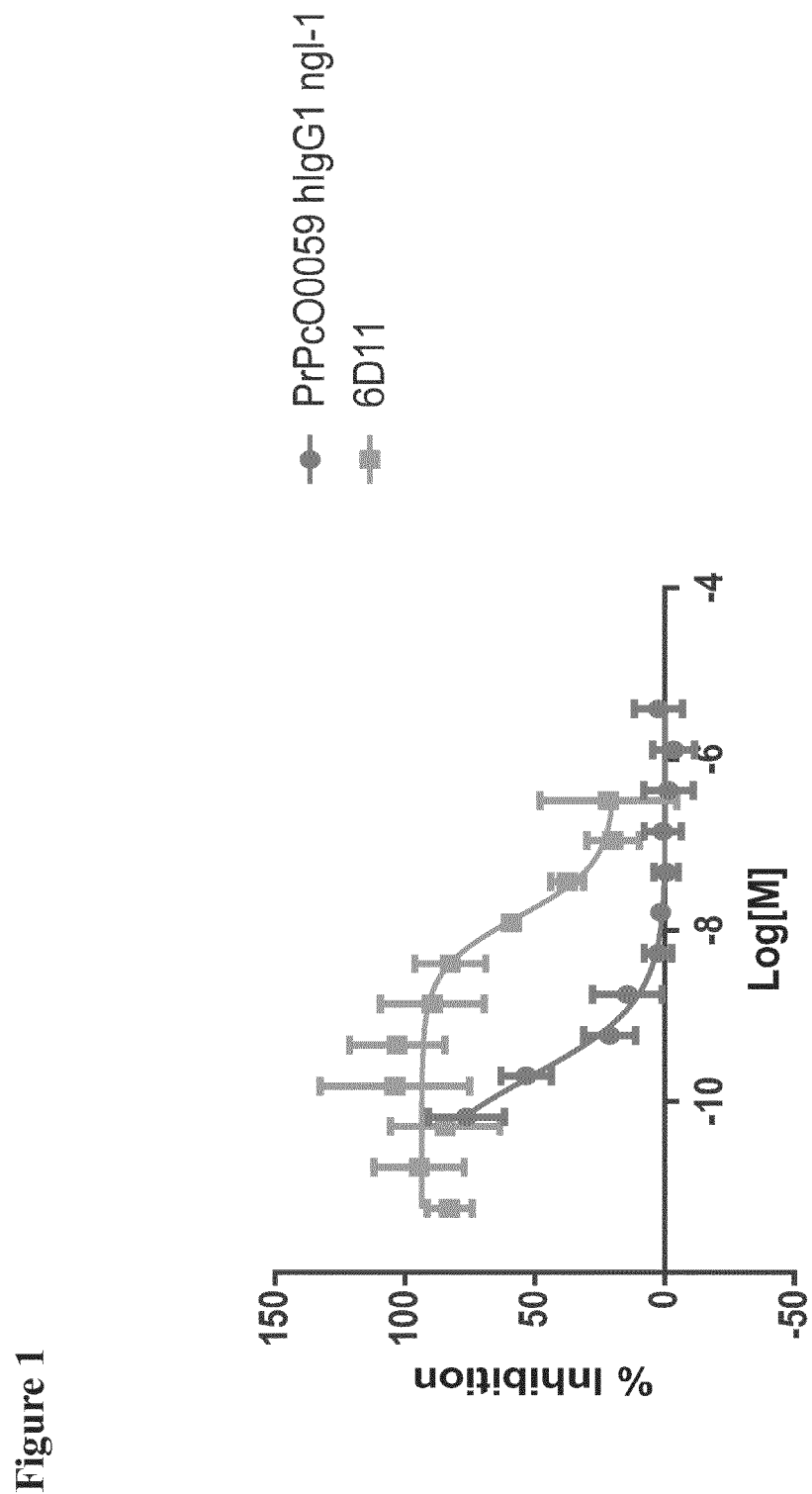
FIG. 1 shows the mean dose-response curves for the representative anti-prion antibody $PrP^C$-O0059 and anti-CD230 (Prion) antibody (6D11) in the epitope competition assay.

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs.

Although any methods and materials similar or equivalent to those described herein can be used in the practice or testing of the present disclosure, the preferred methods and materials are now described.

A. Definitions

As used in this specification and the appended claims, the singular form "a", "an" and "the" include plural referents unless the context clearly dictates otherwise.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Throughout this specification, the word "comprise" or variations such as "comprises" or "comprising" will be understood to imply the inclusion of a stated integer or groups of integers but not the exclusion of any other integer or group of integers.

As used herein, the term "about," when used in reference to a particular recited numerical value, means that the value may vary from the recited value by no more than 10%.

The expressions "prion protein," "PrP$^C$," and the like, as used herein, refer to a human PrP$^C$ protein having an amino acid sequence that is at least 90%, 91%, 92%, 93%, 94%, 95%, 96%, 97%, 98%, 99%, or 100% identical to the amino acid sequence of any of SEQ ID NOs: 1, 2 or 21, or biologically active fragments thereof. In some embodiments, a biologically active fragment of PrP$^C$ protein is capable of binding to the mGluR5 receptor. All references to proteins, polypeptides and protein fragments herein are intended to refer to the human version of the respective protein, polypeptide or protein fragment unless explicitly specified as being from a non-human species (e.g., "mouse PrP$^C$," "monkey PrP$^C$," etc.).

As used herein, "an antibody that binds PrP$^C$", "anti-PrP$^C$ antibody," and the like includes antibodies, and antigen-binding fragments thereof, that bind membrane-bound PrP$^C$ or fragments thereof.

B. Antibodies and Antigen-Binding Fragments Thereof

As used herein, "antibodies or antigen binding fragments of the disclosure" refer to any one or more of the antibodies and antigen binding fragments provided herein. Antibodies and antigen binding fragments of the disclosure comprise a heavy chain comprising a heavy chain variable domain and a light chain comprising a light chain variable domain. A V$_H$ domain comprises three CDRs, such as any of the CDRs provided herein and as defined or identified by the Chothia, Kabat or IMGT systems. These CDRs are typically interspersed with framework regions (FR), and together comprise the V$_H$ domain. Similarly, a VL comprises three CDRs, such as any of the CDRs provided herein and as defined by the Chothia, Kabat or IMGT systems. These CDRs are typically interspersed with framework regions (FR), and together comprise the V$_L$ domain. The FR regions, such as FR1, FR2, FR3, and/or FR4 can similarly be defined or identified by the Chothia, Kabat or IMGT systems. Throughout the application, when CDRs are indicated as being, as identified or as defined by the Chothia, Kabat or IMGT systems, what is meant is that the CDRs are in accordance with that system (e.g., the Chothia CDRs, Kabat CDRs or the IMGT CDRs). Any of these terms can be used to indicate whether the Chothia, Kabat or IMGT CDRs are being referred to.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

In some embodiments, the disclosure provides for an antibody or antigen-binding fragment, wherein the antibody or antigen-binding fragment comprises a light chain variable (VL) domain and a heavy chain variable (VH) domain; wherein the VH domain comprises at least one, two or all three of the CDRs (e.g., as measured using any of the Chothia, IMGT or Kabat systems) of the amino acid sequence set forth in SEQ ID NO: 4. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises CDR1, CDR2 and CDR3 (e.g., as measured using any of the Chothia, IMGT or Kabat systems) of the amino acid sequence set forth in SEQ ID NO: 4. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises at least one, two or all three of the CDRs (e.g., as measured using any of the Chothia, IMGT or Kabat systems) of the amino acid sequence set forth in SEQ ID NO: 13. In some embodiments, the disclosure provides for an antibody or antigen-binding fragment, wherein the antibody or antigen-binding fragment comprises a light chain variable (VL) domain and a heavy chain variable (VH) domain; wherein the VL domain comprises CDR1, CDR2 and CDR3 (e.g., as measured using any of the Chothia, IMGT or Kabat systems) of the amino acid sequence set forth in SEQ ID NO: 13. In some embodiments, the VH domain comprises at least one, two or all three of a VH CDR1 having the amino acid sequence of SEQ ID NO: 5; a VH CDR2 having the amino acid sequence of SEQ ID NO: 6; and a VH CDR3 having the amino acid sequence of SEQ ID NO: 7. In some embodiments, the VH domain comprises a VH CDR1 having the amino acid sequence of SEQ ID NO: 5; a VH CDR2 having the amino acid sequence of SEQ ID NO: 6; and a VH CDR3 having the amino acid sequence of SEQ ID NO: 7. In some embodiments, the VL domain comprises at least one, two or all three of a VL CDR1 having the amino acid sequence of SEQ ID NO: 14; a VL CDR2 having the amino acid sequence of SEQ ID NO: 15; and a VL CDR3 having the amino acid sequence of SEQ ID NO: 16. In some embodiments, the VL domain comprises: a VL CDR1 having the amino acid sequence of SEQ ID NO: 14; a VL CDR2 having the amino acid sequence of SEQ ID NO: 15; and a VL CDR3 having the amino acid sequence of SEQ ID NO: 16. In some embodiments, the VH domain comprises framework regions that are at least 80%, 85%, 90%, 91%, 92%, 93%, 94%, 95%, 96%, 97%, 98%, 99% or 100% identical to the amino acid sequences of SEQ ID NO: 8, SEQ ID NO: 9, SEQ ID NO: 10 and SEQ ID NO: 11. In some embodiments, the VH domain comprises framework regions having the amino acid sequences of SEQ ID NO: 8, SEQ ID NO: 9, SEQ ID NO: 10 and SEQ ID NO: 11. In some embodiments, the VL domain comprises framework regions that are at least 80%, 85%, 90%, 91%, 92%, 93%, 94%, 95%, 96%, 97%, 98%, 99% or 100% identical to the amino acid sequences of SEQ ID NO: 17, SEQ ID NO: 18, SEQ ID NO: 19 and SEQ ID NO: 20. In some embodiments, the VL domain comprises framework regions having the amino acid sequences of SEQ ID NO: 17, SEQ ID NO: 18, SEQ ID NO: 19 and SEQ ID NO: 20. In some embodiments, the VH domain comprises an amino acid sequence that is at least 80%, 85%, 90%, 91%, 92%, 93%, 94%, 95%, 96%, 97%, 98%, 99% or 100% identical to SEQ ID NO: 4. In some embodiments, the VL domain comprises an amino acid sequence that is at least 80%, 85%, 90%, 91%, 92%, 93%, 94%, 95%, 96%, 97%, 98%, 99% or 100% identical to SEQ ID NO: 13.

Once the nucleotide sequences encoding such antibodies have been determined, chimeric or humanized antibodies may be produced by recombinant methods. Nucleic acids encoding the antibodies are introduced into host cells and expressed using materials and procedures generally known in the art, and as disclosed herein. In some embodiments, the antibody or antigen-binding fragment is encoded by a nucleic acid comprising a nucleotide sequence that is at least 80%, 85%, 90%, 91%, 92%, 93%, 94%, 95%, 96%, 97%, 98%, 99% or 100% identity to SEQ ID NO: 3. In some embodiments, the antibody or antigen-binding fragment is encoded by a nucleic acid comprising a nucleotide sequence that is at least 80%, 85%, 90%, 91%, 92%, 93%, 94%, 95%, 96%, 97%, 98%, 99% or 100% identity to SEQ ID NO: 12.

The present disclosure includes anti-$PrP^C$ antibodies and antigen-binding fragments thereof that bind $PrP^C$. In some embodiments, the antibody is a neutralizing and/or blocking anti-$PrP^C$ antibody or antigen-binding fragment. A "neutralizing" or "blocking" antibody or antigen-binding fragment, as used herein, is intended to refer to an antibody or antigen-binding fragment whose binding to $PrP^C$: (i) interferes with the interaction between $PrP^C$ and a glutamate receptor (e.g., mGluR5); (ii) interferes with the interaction between $PrP^C$ and amyloid beta peptide(s) (e.g., soluble amyloid beta peptide oligomers); (iii) interferes with the interaction between $PrP^C$ or a $PrP^C$ fragment with prion protein in a misfolded conformer (e.g., $PrP^{Sc}$ or $PrP^{Sc}$); (iv) interferes with the interaction between $PrP^C$ or a $PrP^C$ fragment with glycosaminoglycans (e.g., sulfated glycans, heparin sulfate, pentosan polysulfate), nucleic acids (e.g., ribonucleic acids such as RNA), metals (e.g., copper, zinc, manganese and/or nickel); and/or lipids (cholesterol); and/or (v) results in inhibition of at least one biological function of $PrP^C$. In some embodiments, the antibodies or antigen-binding fragments of the disclosure inhibit accumulation of $PrP^{Sc}$. In some embodiments, the antibodies or antigen-binding fragments inhibit conversion of $PrP^C$ into $PrP^{Sc}$. In some embodiments, the anti-$PrP^C$ antibodies or antigen-binding fragments of the disclosure inhibit binding of a reference anti-$PrP^C$ antibody to $PrP^C$ protein. In some embodiments, the reference anti-$PrP^C$ antibody is anti-CD230 (Prion) antibody 6D11 Mu IgG2a (BioLegend, San Diego, Calif.). The inhibition caused by a $PrP^C$ neutralizing or blocking antibody need not be complete so long as it is detectable using an appropriate assay. Some examples of assays for detecting activity a representative anti-$PrP^C$ antibody or antigen-binding fragment are described in the working Examples herein. The skilled worker is aware of additional anti-$PrP^C$ antibody activity assays. For example, the skilled worker is aware of representative assays for testing anti-$PrP^{Sc}$ accumulation/conversion both in vitro and in vivo. See, e.g., Shimizu et al., 2010, Microbiol Immunol, 54(2):112-21; White et al., 2003, Nature, 422:80-83; Yamasaki et al., 2014, PLOS One, 9(9): e106516; Jones et al., 2010, PLOS One, 5(3):e9804; Ohsawa et al., 2013, Microbiology and Immunology, 57:288-297), each of which is incorporated by reference in its entirety.

In particular embodiments, any of the antibodies or antigen-binding fragments disclosed herein interferes with the interaction between $PrP^C$ and a glutamate receptor. In some embodiments, the glutamate receptor is mGluR5. In some embodiments, the anti-$PrP^C$ antibodies or antigen-binding fragments block the interaction between $PrP^C$ and a glutamate receptor (e.g., mGluR5) in vitro, with an $IC_{50}$ value of less than about 15 nM, as measured by a binding assay such as that described in Haas et al., 2014, Journal of Biological Chemistry, 289, 28460-28477, or a substantially similar assay. In certain embodiments, the antibodies or antigen-binding fragments of the present disclosure block the interaction between $PrP^C$ and a glutamate receptor (e.g., mGluR5) in vitro with an $IC_{50}$ value of less than about 10 nM, less than about 5 nM, less than about 900 pM, less than about 800 pM, less than about 700 pM, less than about 600 pM, less than about 500 pM, less than about 400 pM, less than about 300 pM, less than about 280 pM, less than about 260 pM, less than about 250 pM, less than about 240 pM, less than about 230 pM, less than about 220 pM, less than about 200 pM, less than about 180 pM, less than about 160 pM, or less than about 150 pM, as measured by a binding assay such as that described in Haas et al., 2014, Journal of Biological Chemistry, 289, 28460-28477, or a substantially similar assay. In some embodiments, the antibodies or antigen-binding fragments prevent abnormal clustering and/or overstabilization of mGluR5 receptors within the plasma membrane. In some embodiments, the antibodies or antigen-binding fragments inhibit/reduce amyloid beta peptide (e.g., soluble amyloid beta peptide oligomers) induced neurotoxicity.

In particular embodiments, any of the antibodies or antigen-binding fragments disclosed herein interfere with the interaction between PrP$^C$ and amyloid beta peptide (e.g., soluble amyloid beta peptide oligomers). In some embodiments, the antibodies prevent amyloid beta peptide (e.g., soluble amyloid beta peptide oligomers) from triggering abnormal clustering and/or overstabilization of mGluR5 receptors within the plasma membrane. In some embodiments, the amyloid beta peptide is Aβ42 oligomers.

The present disclosure provides for anti-PrPC antibodies and antigen-binding fragments thereof that bind PrP$^C$ molecules with high affinity. For example, the present disclosure includes antibodies and antigen-binding fragments of antibodies that bind PrP$^C$ (e.g., at 25° C. or 37° C.) with a $K_D$ of less than about 10 nM. $K_D$ can be measured in accordance with currently standard methods, such as using Surface Plasmon Resonance (SPR) or Quartz Crystal Microbalance (QCM). In certain embodiments, the antibodies or antigen-binding fragments of the present disclosure bind PrP$^C$ with a $K_D$ of less than about 5 nM, less than about 2 nM, less than about 1 nM, less than about 800 pM, less than about 600 pM, less than about 500 pM, less than about 400 pM, less than about 300 pM, less than about 200 pM, less than about 150 pM, less than about 100 pM, less than 50 pM, less than about 30 pM, less than about 25 pM, or less than about 20 pM.

The present disclosure also includes anti-PrP$^C$ antibodies and antigen-binding fragments thereof that specifically bind to PrP$^C$ with a dissociative half-life (t½) of greater than about 10 minutes as measured using an assay such as surface plasmon resonance at 25° C. or 37° C. In certain embodiments, the antibodies or antigen-binding fragments of the present disclosure bind PrP$^C$ with a t½ of greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, as measured by surface plasmon resonance at 25° C. or 37° C.

The antibodies of the present disclosure may possess one or more of the aforementioned biological characteristics, or any combinations thereof. Other biological characteristics of the antibodies of the present disclosure will be evident to a person of ordinary skill in the art from a review of the present disclosure including the working Examples herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In some embodiments, any of the antibodies or antigen-binding fragments disclosed herein comprise 1, 2, 3, 4, 5, 6, 7, 8, 9, 10, 11, 12, 13, 14, 15, 16, 17, 18, 19, or 20 conservative amino acid substitutions as compared to a reference sequence (e.g., any of the the amino acid sequences of SEQ ID NO: 4-11 or 13-20). A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

Non-limiting examples of antigen-binding fragments include: (i) Fab fragments; (ii) Fab' fragments; (iii) F(ab')2 fragments; (iv) Fd fragments; (v) Fv fragments; (vi) single-chain Fv (scFv) molecules; (vii) dAb fragments; and (viii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, cameliid antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain (e.g., at least one of a VH or VL). The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) VH-CH1; (ii) VH-CH2; (iii) VH-CH3; (iv) VH-CH1-CH2; (V) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments, the hinge region comprises a glycine-serine linker.

Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

In some embodiments, the antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity. In some embodiments, the constant region of the antibodies or antigen-binding fragments is not engineered.

In certain embodiments of the disclosure, the anti-PrP$^C$ antibodies of the disclosure are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs, and in some embodiments, CDR3. However, the term "human antibody", as used herein, is not intended to include antibodies in which CDR sequences derived from the germline of another mammalian species, such as a mouse, have been grafted onto human framework sequences.

The antibodies of the disclosure may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG$_4$ hinge can significantly reduce the appearance of the second form (Angal et al. (1993) Molecular Immunology 30:105) to levels typically observed using a human IgG$_1$ hinge. The current disclosure contemplates antibodies having one or more mutations in the hinge, CH2 or CH3 region which may be desirable, for example, in production, to improve the yield of the desired antibody form.

The antibodies of the disclosure may be isolated antibodies or isolated antigen-binding fragments. An "isolated antibody" or "isolated antigen-binding fragment," as used herein, means an antibody or antigen-binding fragment that has been identified and separated and/or recovered from at least one component of its natural environment. For example, an antibody or antigen-binding fragment that has been separated or removed from at least one component of an organism, or from a tissue or cell in which the antibody naturally exists or is naturally produced, is an "isolated antibody" or an "isolated antigen-binding fragment" for purposes of the present disclosure. An isolated antibody also includes an antibody in situ within a recombinant cell. Isolated antibodies or antigen-binding fragments are antibodies or antigen-binding fragments that have been subjected to at least one purification or isolation step. According to certain embodiments, an isolated antibody or antigen-binding fragment may be substantially free of other cellular material and/or chemicals.

The anti-PrP$^C$ antibodies or antigen-binding fragments disclosed herein may comprise one or more amino acid substitutions, insertions and/or deletions in the framework and/or CDR regions of the heavy and light chain variable domains as compared to the corresponding germline sequences from which the antibodies were derived (e.g., PrP$^C$-O0059). Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody or antigen-binding fragment was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes anti-PrP$^C$ antibodies comprising variants of any of the VH, VL, and/or CDR amino acid sequences disclosed herein having one or more conservative substitutions. For example, the present disclosure includes anti-PrP$^C$ antibodies having VH, VL, and/or CDR amino acid sequences with, e.g., 10 or fewer, 8 or fewer, 6 or fewer, 4 or fewer, etc. conservative amino acid substitutions relative to any of the VH, VL, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

It should be noted that any portion of any of the antibodies or antigen-binding fragments of the disclosure may be similarly modified, such as with an epitope tag, a PEG moiety or moieties, and the like. Moreover, the antibodies or antigen-binding fragments may comprise more than one epitope tags, such as 2 epitope tags, or may include 0 epitope tags.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

In some embodiments, the antibody or antigen-binding fragment is an antigen-binding fragment. In some embodiments, the antigen-binding fragment is an scFv. In some embodiments, the antigen-binding fragment is a Fab'. In some embodiments, the antibody or antigen-binding fragment is an antibody. In some embodiments, the antibody is a monoclonal antibody.

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63). In many cases, hybridomas are used to generate an initial antibody of murine or rodent origin. That initial antibody may then be modified, such as using recombinant techniques to produce rodent variants, chimeric antibodies, humanized antibodies and the like. Other methods exist to produce an initial antibody, and such methods are known in the art. However, regardless of the method used to generate an initial antibody or even a variant of that initial antibody, any given antibody of non-human origin can then be modified to increase its humanness.

It can be advantageous to increase the humanness of a non-human antibody to make it more suitable for use in human subject and cells, whether for diagnostic, therapeutic, or research purposes. Antibodies may be modified for use as therapeutics. Examples of such antibodies (including antibody fragments) include chimeric, humanized, and fully human antibodies. Numerous methods exist in the art for the generation of chimeric, humanized and human antibodies. In the context of the present disclosure, an antibody is considered humanized if at least one of the VH domain or VL domain is humanized. Moreover, a VH or VL domain is humanized if the amino acid sequence of at least a portion of at least one of the FR regions has been modified, relative to a parent non-human (e.g., murine) antibody, such that the amino acid sequence of that portion corresponds to that of a human antibody or a human consensus sequence. In certain embodiments, at least one, two, three, or four FR regions of the VH domain and/or at least one, two, three, or four FR regions of the VL domain have been modified (in whole or in part) so that their sequence is more closely related to a human sequence. For any of the foregoing in certain embodiments, a humanized antibody fragment may be provided in the context of a human or non-human light chain and/or heavy chain constant region (e.g., comprising a CL and one or more of a CH1, hinge, CH2, and/or CH3 domains). In certain embodiments, a humanized antibody or antigen binding fragment of the disclosure is provided in the context of human light and/or heavy chain constant domains, when present. Antibodies and antibody binding fragments combining any of the humanized light chain variable domains and/or heavy chain variable domains described herein are exemplary of antibodies and antigen binding fragments of the disclosure. In some embodiments, the antibody or antigen-binding fragment is humanized. In some embodiments, the antibody or antigen-binding fragment is chimeric. In some embodiments, the antibody or antigen-binding fragment is human.

According to certain embodiments of the present disclosure, anti-PrP$^C$ antibodies are provided comprising an Fc domain comprising one or more mutations which enhance or diminish antibody binding to the FcRn receptor, e.g., at acidic pH as compared to neutral pH. For example, the present disclosure includes anti-PrP$^C$ antibodies comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., D297A) modification. Additional Fc modifications may include, for example, L234F, L235E and/or P331S. See, e.g., Oganesyan et al., 2008, Acta Crystallogr D Biol Crystallogr., 64(Pt 6):700-704. All possible combinations of the foregoing Fc domain mutations, and other mutations within the antibody variable domains disclosed herein, are contemplated within the scope of the present disclosure.

The present disclosure also includes anti-PrP$^C$ antibodies comprising a chimeric heavy chain constant (CH) region, wherein the chimeric CH region comprises segments derived from the CH regions of more than one immunoglobulin isotype. For example, the antibodies of the disclosure may comprise a chimeric CH region comprising part or all of a CH2 domain derived from a human IgG$_1$, human IgG$_2$ or human IgG$_4$ molecule, combined with part or all of a CH3 domain derived from a human IgG$_1$, human IgG$_2$ or human IgG$_4$ molecule. According to certain embodiments, the antibodies of the disclosure comprise a chimeric CH region having a chimeric hinge region. For example, a chimeric hinge may comprise an "upper hinge" amino acid sequence (amino acid residues from positions 216 to 227 according to EU numbering) derived from a human IgG$_1$, a human IgG$_2$ or a human IgG$_4$ hinge region, combined with a "lower hinge" sequence (amino acid residues from positions 228 to 236 according to EU numbering) derived from a human IgG$_1$, a human IgG$_2$ or a human IgG$_4$ hinge region. According to certain embodiments, the chimeric hinge region comprises amino acid residues derived from a human IgG$_1$ or a human IgG$_4$ upper hinge and amino acid residues derived from a human IgG$_2$ lower hinge. An antibody comprising a chimeric CH region as described herein may, in certain embodiments, exhibit modified Fc effector functions without adversely affecting the therapeutic or pharmacokinetic properties of the antibody. (See, e.g., US 2015-0203591 A1).

The present disclosure includes anti-PrP$^C$ antibodies which interact with one or more amino acids of PrP$^C$. For example, the present disclosure includes anti-PrP$^C$ antibodies that interact with one or more amino acids located within amino acids 91-153 of SEQ ID NOs: 1 or 2. In some embodiments, the present disclosure includes anti-PrP$^C$ antibodies that interact with one or more amino acids located within amino acids 23-111 of SEQ ID NOs: 1 or 2. In particular embodiments, the anti-PrP$^C$ antibodies interact with one or more amino acids located within amino acids 90-111 of SEQ ID NOs: 1 or 2. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids of PrP$^C$. Alternatively, the epitope may consist of a plurality of non-contiguous amino acids (or amino acid sequences) of PrP$^C$.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267 (2):252-259; Engen and Smith (2001) Anal. Chem. 73:256A-265A.

The present disclosure further includes anti-PrP$^C$ antibodies or antigen-binding fragments thereof that bind to the same epitope as any of the antibodies or antigen-binding fragments described herein (e.g., an antibody or antigen-binding fragment comprising the amino acid sequences of SEQ ID NOs: 4 and 13). Likewise, the present disclosure also includes anti-PrP$^C$ antibodies and antigen-binding fragments that compete for binding to PrP$^C$ with any of the antibodies or antigen-binding fragments described herein (e.g., an antibody or antigen-binding fragment comprising the amino acid sequences of SEQ ID NOs: 4 and 13). In some embodiments, the present disclosure provides for anti-PrP$^C$ antibodies and antigen-binding fragments that compete for binding to PrP$^C$ with the 6D11 antibody. In some embodiments, the anti-PrP$^C$ antibodies and antigen-binding fragments bind PrP$^C$ with a tighter affinity than the binding affinity of the 6D11 antibody for PrP$^C$. The skilled worker can easily determine whether an antibody binds to the same epitope as, or competes for binding with, a reference anti-PrP$^C$ antibody by using routine methods known in the art and exemplified herein. For example, to determine if a test antibody binds to the same epitope as a reference anti-PrP$^C$ antibody of the disclosure, the reference antibody is allowed to bind to a PrP$^C$ protein. Next, the ability of a test antibody to bind to the PrP$^C$ molecule is assessed. If the test antibody is able to bind to PrP$^C$ following saturation binding with the reference anti-PrP$^C$ antibody, it can be concluded that the test antibody binds to a different epitope than the reference anti-PrP$^C$ antibody. On the other hand, if the test antibody is not able to bind to the PrP$^C$ molecule following saturation binding with the reference anti-PrP$^C$ antibody, then the test antibody may bind to the same epitope as the epitope bound by the reference anti-PrP$^C$ antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502).

Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-PrP$^C$ antibody, the above-described binding methodology is performed in two orientations: In a first orientation, the reference antibody is allowed to bind to a PrP$^C$ protein under saturating conditions followed by assessment of binding of the test antibody to the PrP$^C$ molecule. In a second orientation, the test antibody is allowed to bind to a PrP$^C$ molecule under saturating conditions followed by assessment of binding of the reference antibody to the PrP$^C$ molecule. If, in both orientations, only the first (saturating) antibody is capable of binding to the PrP$^C$ molecule, then it is concluded that the test antibody and the reference antibody compete for binding to PrP$^C$. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Methods for generating monoclonal antibodies, including fully human monoclonal antibodies are known in the art. Any such known methods can be used in the context of the present disclosure to make human antibodies that specifically bind to human PrP$^C$.

Using VELOCIMMUNE™ technology, for example, or any other known method for generating fully human monoclonal antibodies, high affinity chimeric antibodies to PrP$^C$ are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified IgG$_1$ or IgG$_4$, to generate a fully human anti-PrP$^C$ antibody. While the constant region selected may vary according to specific use, high affinity antigen-binding and target specificity characteristics reside in the variable region. In certain instances, fully human anti-PrP$^C$ antibodies are isolated directly from antigen-positive B cells.

The anti-PrP$^C$ antibodies and antibody fragments of the present disclosure encompass proteins having amino acid sequences that may vary from those of the described antibodies but that retain the ability to bind PrP$^C$ (e.g., SEQ ID NOs: 1, 2 and 21). Such variant antibodies and antibody fragments comprise one or more additions, deletions, or substitutions of amino acids when compared to parent sequence, but exhibit biological activity that is essentially equivalent to that of the described antibodies. Likewise, the anti-PrP$^C$ antibody-encoding DNA sequences of the present disclosure encompass sequences that comprise one or more additions, deletions, or substitutions of nucleotides when compared to the disclosed sequences, but that encode an anti-PrP$^C$ antibody or antibody fragment that is essentially bioequivalent to an anti-PrP$^C$ antibody or antibody fragment of the disclosure. Examples of such variant amino acid and DNA sequences are discussed above.

Two antibodies or antigen-binding fragments are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies or antigen-binding fragments will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two antibodies or antigen-binding fragments are bioequivalent if there are no clinically meaningful differences in their safety, purity, and potency.

In some embodiments, two antibodies or antigen-binding fragments are bioequivalent if a patient can be switched one or more times between the reference product and the biological product without an expected increase in the risk of adverse effects, including a clinically significant change in immunogenicity, or diminished effectiveness, as compared to continued therapy without such switching.

In some embodiments, two antibodies or antigen-binding fragments are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PrP$^C$ antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies or antigen-binding fragments may include anti-$PrP^C$ antibody variants comprising amino acid changes which modify the glycosylation characteristics of the antibodies or antigen-binding fragments, e.g., mutations which eliminate or remove glycosylation.

The present disclosure, according to certain embodiments, provides anti-$PrP^C$ antibodies or antigen-binding fragments that bind to human $PrP^C$ but not to $PrP^C$ from other species. The present disclosure also includes anti-$PrP^C$ antibodies that bind to human $PrP^C$ and to $PrP^C$ from one or more non-human species. For example, the anti-$PrP^C$ antibodies of the disclosure may bind to human $PrP^C$ and may bind or not bind, as the case may be, to one or more of mouse, rat, guinea pig, hamster, gerbil, pig, cat, dog, rabbit, goat, sheep, cow, horse, camel, cynomolgus monkey, marmoset, rhesus or chimpanzee $PrP^C$. According to certain exemplary embodiments of the present disclosure, anti-$PrP^C$ antibodies or antigen binding fragments are provided which specifically bind human $PrP^C$ and cynomolgus monkey (e.g., Macaca fascicularis) $PrP^C$. In particular embodiments, the antibodies or antigen-binding fragments of the disclosure bind human, rat, mouse and cynomolgus monkey $PrP^C$ protein.

The disclosure encompasses anti-$PrP^C$ monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

In some embodiments, the antibodies of the present disclosure may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer ei a/., 2004, Trends Biotechnol. 22:238-244. The anti-$PrP^C$ antibodies of the present disclosure can be linked to or co-expressed with another functional molecule, e.g., another peptide or protein. For example, an antibody or antigen-binding fragment thereof can be functionally linked (e.g., by chemical coupling, genetic fusion, noncovalent association or otherwise) to one or more other molecular entities, such as another antibody or antigen-binding fragment to produce a bi-specific or a multispecific antibody with a second binding specificity. For example, the present disclosure includes bi-specific antibodies wherein one arm of an immunoglobulin is specific for human $PrP^C$ or a fragment thereof, and the other arm of the immunoglobulin is specific for a second therapeutic target or is conjugated to a therapeutic moiety.

An exemplary bi-specific antibody or antigen-binding fragment format that can be used in the context of the present disclosure involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT;

Y436F by EU). Further modifications that may be found within the second CH3 include: D16E, L18M, N44S, K52N, V57M, and V82I (by IMGT; D356E, L358M, N384S, K392N, V397M, and V422I by EU) in the case of lgG1 antibodies; N44S, K52N, and V82I (IMGT; N384S, K392N, and V422I by EU) in the case of lgG2 antibodies; and Q15R, N44S, K52N, V57M, R69K, E79Q, and V82I (by IMGT; Q355R, N384S, K392N, V397M, R409K, E419Q, and V422I by EU) in the case of lgG4 antibodies. Variations on the bi-specific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-lg, Quadroma, knobs-into-holes, common light chain (e.g., common light chain with knobs-into-holes, etc.), CrossMab, CrossFab, (SEED) body, leucine zipper, Duobody, lgG1/lgG2, dual acting Fab (DAF)-lgG, and Mab<2> bispecific formats (see, e.g., Klein et al. 2012, mAbs 4:6, 1-1 1, and references cited therein, for a review of the foregoing formats). Bispecific antibodies or antigen-binding fragments can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. C em. Soc. [Epub: Dec. 4, 2012]).

C. Nucleic Acids and Expression Systems

In some embodiments, the disclosure provides for a nucleic acid capable of expressing any of the antibodies of antigen-binding fragments disclosed herein. The nucleic acids may be single-stranded or double-stranded, DNA or RNA molecules. In further embodiments, the antibody or antigen-binding fragment nucleic acid sequences can be isolated, recombinant, and/or fused with a heterologous nucleotide sequence, or in a DNA library. In some embodiments, the nucleic acid comprises a nucleotide sequence that is at least 80%, 85%, 90%, 91%, 92%, 93%, 94%, 95%, 96%, 97%, 98%, 99% or 100% identical to SEQ ID NO: 3. In some embodiments, the nucleic acid comprises a nucleotide sequence that is at least 80%, 85%, 90%, 91%, 92%, 93%, 94%, 95%, 96%, 97%, 98%, 99% or 100% identical to SEQ ID NO: 12.

In certain embodiments, nucleic acids encoding antibodies or antigen-binding fragments also include nucleotide sequences that hybridize under highly stringent conditions to a polynucleotide encoding any of the above-mentioned antibodies or antigen-binding fragments nucleotide sequence, or complement sequences thereof. In some embodiments, the nucleic acids hybridize under highly stringent conditions to a polynucleotide encoding an amino acid sequence that is at least 80%, 85%, 90%, 91%, 92%, 93%, 94%, 95%, 96%, 97%, 98%, 99% or 100% identical to SEQ ID NO: 4 or 13. In some embodiments, the nucleic acids hybridize under highly stringent conditions to a polynucleotide having the nucleotide sequence of SEQ ID NO: 3 or 12. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids encoding the antibody or antigen-binding fragment thereof due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In some embodiments, the disclosure provides for a vector comprising any of the nucleic acids disclosed herein. In some embodiments, the disclosure provides for a host cell comprising any of the vectors disclosed herein.

Regardless of when an antibody of the disclosure is a full length antibody or an antigen binding fragment, antibodies and antigen binding fragments of the disclosure can be recombinantly expressed in cell lines. In these embodiments, sequences encoding particular antibodies or antigen binding fragments can be used for transformation of a suitable host cell, such as a mammalian host cell or yeast host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the disclosure, a nucleic acid molecule encoding the amino acid sequence of a heavy chain constant region (all or a portion), a heavy chain variable region of the disclosure, a light chain constant region, or a light chain variable region of the disclosure is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, Meth. Enzymol. Vol. 185, Academic Press. N.Y. In the context of antibody expression, both the heavy and light chain may be expressed from the same vector (e.g., from the same or different promoters present on the same vector) or the heavy and light chains may be expressed from different vectors. In certain embodiments, the heavy and light chains are expressed from different vectors which are transfected into the same host cell and co-expressed. Regardless of when the heavy and light chains are expressed in the same host cell from the same or a different vector, the chains can then associate to form an antibody (or antibody fragment, depending on the portions of the heavy and light chain being expressed).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These portions of vectors are well known, and there are numerous generally available vectors that can be selected and used for the expression of proteins. One can readily select vectors based on the desired host cell and application.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

The expression and cloning vectors of the disclosure will typically contain a promoter that is recognized by the host organism and operably linked to the molecule encoding heavy and/or light chain. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the heavy chain or light chain comprising an antibody or antigen binding fragment of the disclosure. In certain embodiments, the same promoter is used for both the heavy and light chain. In other embodiments, different promoters (present on the same or different vectors) are used for each.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, Nature 290:304-10); the CMV promoter; the promoter contained in the 3' long terminal repeat of Rous sarcoma virus (Yamamoto et al., 1980, Cell 22:787-97); the herpes thymidine kinase promoter (Wagner et al., 1981, Proc. Natl. Acad. Sci. USA 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. USA 75:3727-31); or the tac promoter (DeBoer et al., 1983, Proc. Natl. Acad. Sci. USA 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol. 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol. 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:338-40; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

The vector may also include an enhancer sequence to increase transcription of DNA encoding light chain or heavy chain.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an antibody or antigen binding fragment of the disclosure has been inserted into the proper site of the vector, the completed vector may be inserted into a suitable host cell for amplification and/or polypeptide expression. The transformation of an expression vector into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled worker.

The host cell, when cultured under appropriate conditions, synthesizes the antibody or antigen binding fragment of the disclosure that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as host cells for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, one may select a cell line from the B cell lineage that does not make its own antibody but has a capacity to make and secrete a heterologous antibody (e.g., mouse myeloma cell lines NS0 and SP2/0). In other embodiments, a cell other than a mammalian cell is used, such as a yeast cell line (e.g., *Pichia*).

In certain embodiments, the cell line stably expresses an antibody or antigen binding fragment of the disclosure. In other embodiments, the cells transiently express an antibody or antigen binding fragment of the disclosure.

D. Therapeutic Formulation and Administration

The disclosure provides pharmaceutical compositions comprising the anti-$PrP^C$ antibodies or antigen-binding fragments thereof of the present disclosure. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-31 1.

The dose of antibody administered to a patient may vary depending upon the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering anti-$PrP^C$ antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intrathecal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In some embodiments, the antibodies and antigen-binding fragments thereof have utility in treating conditions and disorders associated with the central nervous system, and, particularly associated with the brain. While various factors must be considered when administering a macromolecule such as an antibody or antigen-binding fragment to a subject's brain, i.e., ability of the antibody or antigen-binding fragment to cross the blood-brain-barrier (BBB), the skilled worker is aware of methods of administering such macromolecules to the brain. For example, in some embodiments, the antibody or antigen-binding fragment is covalently modified with one or more cationic polyamines, such as hexamethylenediamine or tetramethylenediamine in order to increase the likelihood that the antibody or antigen-binding fragment is internalized across the BBB. In some embodiments, the antibody or antigen-binding fragment is a bispecific antibody or antigen-binding fragment, wherein the antibody or fragment targets $PrP^C$ and also targets a receptor that facilitates transport across the BBB (e.g., transferrin receptor, insulin receptor and TMEM30A). In some embodiments, the antibody or antigen-binding fragment is conjugated to an agent that targets a receptor that facilitates transport across the BBB (e.g., transferrin receptor, insulin receptor and TMEM30A). In some embodiments, the BBB is temporarily disrupted prior to or during administration of the antibody or fragment. In some embodiments the BBB is temporarily disrupted by means of ultrasound, radiation, biochemical treatment (e.g., with a $K_{Ca}$ receptor agonist such as NS-1619), or intra-arterial infusion of concentrated hyperosmotic solutions.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intrathecal, intracutaneous and intramuscular injections, drip infusions, etc. These injectable preparations may be prepared by methods publicly known. For example, the injectable preparations may be prepared, e.g., by dissolving, suspending or emulsifying any of the antibodies or antigen-binding fragments disclosed herein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody or antigen-binding fragment is contained in about 5 to about 100 mg and in about 10 to about 250 mg for the other dosage forms.

E. Therapeutic Uses of the Antibodies

For any of the methods described herein, the disclosure contemplates the use of any of the antibodies or antigen-binding fragments of the disclosure.

In some embodiments, the disclosure provides for a method of treating a disease or disorder associated with amyloid β (Aβ) accumulation. In some embodiments, the Aβ includes any one or more of Aβ1-42, pGluAβ3-42, Aβ3-42 or Aβ4-42. In some embodiments, the Aβ includes Aβ1-42 or Aβ4-42. In some embodiments, the Aβ is in the form of oligomers.

In some embodiments, the disclosure provides for a method of treating a neurodegenerative disorder in a subject in which aberrant $PrP^C$ activity is involved, comprising administering any of the antibodies or antigen-binding fragments described herein. As used herein, "disorder", "condition" and "disease" are used interchangeably to refer to any of the disorders, conditions or diseases disclosed herein. Examples of disorders in which aberrant $PrP^C$ activity is involved include Alzheimer's Disease, Iatrogenic Creutzfeldt-Jakob Disease (CJD), Variant Creutzfeldt-Jakob Disease (vCJD), Familial CJD, Sporadic CJD, Gerstmann-Straussler-Scheinker Syndrome, Fatal Familial Insomnia, Kuru, Alpers Syndrome (progressive sclerosing poliodystrophy), Bovine Spongiform Encephalopathy (BSE), Chronic Wasting Disease (CWD), Scrapie, Transmissible mink encephalopathy, Feline spongiform encephalopathy, Ungulate spongiform encephalopathy, amyotrophic lateral sclerosis (ALS), frontotemporal lobar degeneration with ubiquitin-positive inclusions (FTLD-U), sporadic or familial Alzheimer's disease, and Huntington's disease, multisystem proteinopathy (MSP), Systemic Amyloidosis including AA (Secondary) Amyloidosis that develops in humans and animals with inflammatory and infectious diseases such as Tuberculosis, Crohn's disease, Rheumatoid arthritis, and HIV AIDS. In some embodiments, the disorder is Alzheimer's Disease, Iatrogenic Creutzfeldt-Jakob Disease (CJD), Variant Creutzfeldt-Jakob Disease (vCJD), Familial CJD, Sporadic CJD, Gerstmann-Straussler-Scheinker Syndrome, Fatal Familial Insomnia or Kuru. In particular embodiments, the disorder is Alzheimer's Disease. Alzheimer's Disease occurs three to five times more often among people with Down Syndrome than the general population. People with Down Syndrome are also more likely to develop Alzheimer's Disease at a younger age than other adults. In some embodiments, the disorder is Down Syndrome.

In some embodiments, the subject administered any of the antibodies or antigen-binding fragments disclosed herein is a mammal. In some embodiments, the subject is a human. However, as the antibodies and antigen-binding fragments of the disclosure were found to differ from antibodies such as 6D11 in that the antibodies and antigen-binding fragments of the disclosure bind $PrP^C$ from species other than humans (e.g., cynomolgus monkey $PrP^C$), the antibodies and antigen-binding fragments may also be useful in treating non-human animals, e.g., in a veterinary context. Indeed, there are numerous prion-related disorders that exist in non-human animals, including, for example, bovine spongiform encephalopathy, scrapie, chronic wasting disease, feline spongiform encephalopathy and transmissible mink encephalopathy. As such, in some embodiments, the subject to be treated with any of the antibodies or antigen-binding fragments disclosed herein is a non-human animal. In some embodiments, the non-human animal may be selected from any one or more of the following animals: non-human primates (e.g., monkeys, apes), ungulates, cow, sheep, ram, goat, deer, elk, cat, and mink.

In some embodiments, the disclosure provides for a method of interfering with the interaction between $PrP^C$ and a glutamate receptor (e.g., mGluR5) in a cell, comprising the step of administering any of the antibodies or antigen-binding fragments described herein to a cell. In some embodiments, the cell has been exposed to amyloid-beta proteins (amyloid beta peptide oligomers). In some embodiments, the disclosure provides for a method of reducing toxic or detrimental effects in a cell that has been exposed to amyloid-beta proteins (e.g., amyloid-beta peptide oligomers), comprising administering to the cell any of the antibodies or antigen-binding fragments described herein. In some embodiments, the disclosure provides for a method of reducing aberrant glutamate receptor (e.g., mGluR5) signaling in a cell, comprising administering to the cell any of the antibodies or antigen-binding fragments described herein. In some embodiments, the cell is a neuron. In some embodiments, the cell is in vitro. In other embodiments, the cell is in a subject. In some embodiments, the subject is a mammal. In some embodiments, the subject is a human. In some embodiments, the subject suffers from any of disorders disclosed herein. In particular embodiments, the subject suffers from Alzheimer's Disease.

For any of the methods described herein, the disclosure contemplates the combination of any step or steps of one method with any step or steps from another method. These methods involve administering to an individual in need thereof an effective amount of a compound of the disclosure appropriate for the particular disease or condition. In specific embodiments, these methods involve delivering any of the antibodies or antigen-binding fragments disclosed herein to the cells of a subject in need thereof.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes any one or more of: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). For example, "treatment" of Alzheimer's Disease encompasses a complete reversal or cure of the disease, or any range of improvement in conditions and/or adverse effects attributable to Alzheimer's Disease. Merely to illustrate, "treatment" of Alzheimer's Disease includes an improvement in any of the following effects associated with Alzheimer's Disease or combination thereof: mental decline, mental confusion, delusion, disorientation, forgetfulness, difficulty concentrating, inability to create new memories, aggression, agitation, irritability, personality changes, lack of restraint, anger, apathy, general discontent, loneliness, mood swings, depression, hallucination, paranoia, loss of appetite, restlessness, inability to combine muscle movements, jumbled speech, synaptic impairment, neuronal loss, amyloid beta accumulation, tau hyperphosphorylation, accumulation of tau protein, amyloid plaque formation, and neurofibrillary tangle formation. Improvements in any of these conditions can be readily assessed according to standard methods and techniques known in the art. Other symptoms not listed above may also be monitored in order to determine the effectiveness of treating neurodegenerative disease, such as Alzheimer's Disease. The population of subjects treated by the method of the disease includes subjects suffering from the undesirable condition or disease, as well as subjects at risk for development of the condition or disease.

Patients amenable to treatment include patients showing symptoms and also individuals at risk of disease but not showing symptoms. For Alzheimer's disease, potentially anyone is at risk if he or she lives for a sufficiently long time. Any of the antibodies or antigen-binding fragments disclosed herein may be administered prophylactically to a subject without any assessment of the risk of the subject patient. Patients amenable to treatment include individuals who have a known genetic risk of Alzheimer's disease, for example individuals who have blood relatives with this disease and those whose risk is determined by analysis of genetic or biochemical markers. Genetic markers of predisposition towards Alzheimer's disease include mutations in the APP gene, particularly mutations at position 717 and positions 670 and 671 referred to as the Hardy and Swedish mutations, respectively. Other markers of risk are mutations in the presenilin genes, PS1 and PS2, and ApoE4, a family history of Alzheimer's disease, hypercholesterolemia or atherosclerosis. Individuals suffering from Alzheimer's disease can be diagnosed by the characteristic dementia associated with the disease, as well as by the presence of risk factors described above. A number of diagnostic tests are available to assist in identification Alzheimer's disease in an individual. These include measurement of CSF tau and Aβ1-42 levels. Elevated tau and decreased Aβ1-42 levels may signify the presence of Alzheimer's disease. Individuals suffering from Alzheimer's disease can also be diagnosed by NINCDS-ADRDA or DSM-IV-TR criteria. In some embodiments, the Alzheimer's Disease to be treated is mild (early-stage), moderate (middle-stage), or severe (late-stage) Alzheimer's Disease.

In asymptomatic patients, treatment can begin at any age (e.g., at least 10, 20, 30 years of age). Generally, treatment is commenced in later life, for example when a patient reaches his or her 40's, 50's, 60's or 70's. Treatment may involve multiple doses over a period of time, which may be for the duration of the remaining life of the patient. The need for administration of repeat doses can be monitored by measuring antibody levels over time. As Alzheimer's Disease may have an early onset in Down Syndrome patients, administration of any of the antibodies or antigen-binding fragments disclosed herein may be initiated at earlier stages of life (e.g., when the patient is at least 10, 20, 30 years of age) than in a non-Down Syndrome patient.

For prophylaxis, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic, cognitive impairment and/or behavioural symptoms of the disease, its complications and intermediate pathological phenotypes presenting during development of the disease. For therapeutic applications, compositions or medicaments are administered to a patient suspected of, or already suffering from such a disease in an amount sufficient to cure, or at least partially arrest, the symptoms of the disease (biochemical, histologic, cognitive impairment and/or behavioural), including its complications and intermediate pathological phenotypes in development of the disease.

For any of the methods described herein, the disclosure contemplates the use of any of the antibodies or antigen-binding fragments described throughout the application. In addition, for any of the methods described herein, the disclosure contemplates the combination of any step or steps of one method with any step or steps from another method.

In certain embodiments, the present invention provides methods of treating conditions associated with any of the neurodegenerative disorders disclosed herein, e.g., Alzheimer's Disease. These methods involve administering to the individual a therapeutically effective amount of any of the antibodies or antigen-binding fragments as described above. These methods are particularly aimed at therapeutic and prophylactic treatments of animals, and more particularly, humans. The disclosure contemplates all combinations of any of the foregoing aspects and embodiments, as well as combinations with any of the embodiments set forth in the detailed description and examples.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, any of the antibodies or antigen-binding fragments of the present invention can be administered alone or in combination with one or more additional compounds or therapies for treating any of the neurodegenerative disorders disclosed herein (e.g., Alzheimer's Disease). For example, any of the antibodies or antigen-binding fragments disclosed herein can be co-administered in conjunction with one or more therapeutic compounds. When co-administration is indicated, the combination therapy may encompass simultaneous or alternating administration. In addition, the combination may encompass acute or chronic administration. Optionally, the antibody/antigen-binding fragment and additional compounds act in an additive or synergistic manner for treating any of the neurodegenerative disorders disclosed herein (e.g., Alzheimer's Disease). Additional compounds to be used in combination therapies include, but are not limited to, small molecules, polypeptides, antibodies, antisense oligonucleotides, and siRNA molecules. In some embodiments, the additional compound is any one or more of: donepezil (Aricept), galantamine (Razadyne), memantine (Namenda), rivastigmine (Exelon), or tacrine (Cognex). In some embodiments, the additional compound is an antidepressant, an anxiolytic, an antipsychotic, or a sleeping aid. Depending on the nature of the combinatory therapy, administration of the antibodies or antigen binding disclosures of the disclosure may be continued while the other therapy is being administered and/or thereafter. Administration of the antibodies or antigen-binding fragments may be made in a single dose, or in multiple doses. In some instances, administration of the antibodies or antigen binding fragments is commenced at least several days prior to the other therapy, while in other instances, administration is begun either immediately before or at the time of the administration of the other therapy. In some embodiments, any of the additional compounds disclosed herein is conjugated to any of the antibodies or antigen-binding fragments disclosed herein.

In another example of combination therapy, any of the antibodies or antigen-binding fragments of the disclosure can be used as part of a therapeutic regimen combined with one or more additional treatment modalities. By way of example, such other treatment modalities include, but are not limited to, memory training exercises, memory aids, cognitive training, dietary therapy, occupational therapy, physical therapy, psychiatric therapy, massage, acupuncture, acupressure, mobility aids, assistance animals, and the like.

Note that although the antibodies or antigen-binding fragments described herein can be used in combination with other therapies, in certain embodiments, an antibody or antigen-binding fragment is provided as the sole form of therapy. Regardless of whether administrated alone or in combination with other medications or therapeutic regiments, the dosage, frequency, route of administration, and timing of administration of the antibodies or antigen-binding fragments is determined by a physician based on the condition and needs of the patient.

According to certain embodiments of the present disclosure, multiple doses of an anti-$PrP^C$ antibody or antigen-binding fragment thereof (or a pharmaceutical composition comprising a combination of an anti-$PrP^C$ antibody and any of the additional therapies mentioned herein) may be administered to a subject over a defined time course. The methods according to this aspect of the disclosure comprise sequentially administering to a subject multiple doses of an anti-$PrP^C$ antibody or antigen-binding fragment of the disclosure. As used herein, "sequentially administering" means that each dose of anti-$PrP^C$ antibody or antigen-binding fragment is administered to the subject at a different point in time, e.g., on different days separated by a predetermined interval (e.g., hours, days, weeks or months). The present disclosure includes methods which comprise sequentially administering to the patient a single initial dose of an anti-$PrP^C$ antibody or antigen-binding fragment, followed by one or more secondary doses of the anti-$PrP^C$ antibody or antigen-binding fragment, and optionally followed by one or more tertiary doses of the anti-$PrP^C$ antibody or antigen-binding fragment.

The terms "initial dose," "secondary doses," and "tertiary doses," refer to the temporal sequence of administration of the anti-$PrP^C$ antibody or antigen-binding fragment of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-$PrP^C$ antibody, but generally may differ from one another in terms of frequency of administration. In certain embodiments, however, the amount of anti-$PrP^C$ antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

F. Diagnostic/Other Uses of the Antibodies or Antigen Binding Fragments

The anti-$PrP^C$ antibodies of the present disclosure may also be used to detect and/or measure $PrP^C$, or $PrP^C$- expressing cells in a sample, e.g., for diagnostic purposes. For example, an anti-PrP$^C$ antibody, or antigen-binding fragment thereof, may be used to diagnose a condition or disease characterized by aberrant expression (e.g., overexpression, under-expression, lack of expression, etc.) of PrP$^C$. Exemplary diagnostic assays for PrP$^C$ may comprise, e.g., contacting a sample obtained from a patient, with an anti-PrP$^C$ antibody of the disclosure, wherein the anti-PrP$^C$ antibody is labeled with a detectable label or reporter molecule.

Alternatively, an unlabeled anti-PrPC antibody can be used in diagnostic applications in combination with a secondary antibody which is itself detectably labeled. The detectable label or reporter molecule can be a radioisotope, such as $^3$H, $^{14}$C, $^{32}$P, $^{35}$S or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure PrP$^C$ in a sample include enzyme-linked immunosorbent assay (ELISA), radioimmunoassay (RIA), and fluorescence-activated cell sorting (FACS).

The compositions of the disclosure have numerous uses. For example, the antibodies and antigen binding fragments of the disclosure are useful for studying preferential cell and tissue distribution in cells and in tissues in vitro and/or in vivo. Similarly, the humanized antibodies and antigen binding fragments, either alone or conjugated to a heterologous agent are useful as imaging agents, such as for ex vivo or in vivo diagnostic applications. For example, the humanized antibodies or antigen binding fragments conjugated to a radioactive moiety are useful for ex vivo or in vivo imaging studies. Similarly, any of the antibodies or antigen binding fragments of the disclosure are similarly useful.

When used in vitro, the antibodies and antigen binding fragments of the disclosure are suitable for identifying binding partners for the antibody or antigen binding fragment being delivered (e.g., identifying proteins or peptides that bind the antibody or antigen binding fragment), and for evaluating localization and trafficking. Similarly, when used in vivo, the antibodies or antigen-binding fragments are useful for identifying binding partners for the antibody or antigen-binding fragment being delivered (e.g., identifying proteins or peptides that bind the antibody or antigen-binding fragment), for evaluating localization and trafficking, for evaluating biodistribution and half-life, and for evaluating immunogenicity.

G. Animal/Cell Models

Numerous neurodegenerative animal models are known to the skilled worker. For example, the APP/PS1 Tg mice carry a Swedish K670L/M671L APP mutation and a presenilin 1 M146L mutation. By 8 months of age these APP/PS1 Tg mice already have abundant Aβ deposition in the form of plaques and display impaired cognitive ability. See, e.g., Chung et al., 2010, BMC Neurosci, 11:130. The effect of any of the antibodies or antigen-binding fragments disclosed herein on various parameters such as cognitive ability, neuronal loss, neuronal activity, plaque or tangle formation, synaptophysin immunoreactivity may be assessed using methods known in the art. See, e.g., Chung et al. Other models in which any of the antibodies or antigen-binding fragments described herein may be tested may include, for example, various known Alzheimer's Disease mouse models (e.g., PDAPP, TG2576, APP23, TgCRND8, J20, APP/PS1, APP+PS1, APP/PS1 KI, 5×FAD, 3×Tg-AD, or NL-F/NL-F) and/or prion disease mouse models (e.g., Tg2669, Tg35, Tg1, Tg650, HuMM, Tg152, HuVV, Tg4053 and/or Tg338).

Numerous cell/tissue models used for studying neurodegenerative disorders are also known to the skilled worker. For example, the skilled worker could use tissue or cells (e.g., hippocampal slices, as described in Lauren et al., 2009, Nature, 457(7233):1128-32) from any known animal model of neurodegenerative diseases (e.g., Alzheimer's Disease) to study the effects of any of the antibodies or antigen binding fragments disclosed herein.

H. Kits

In certain embodiments, the invention also provides a pharmaceutical package or kit comprising one or more containers filled with at least one antibody or antigen-binding fragment of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Synthesis of a Representative Anti-PrP$^C$ Antibody

A representative Anti-PrP$^C$ antibody (referred to as "PrP$^c$-0123" herein) was synthesized by performing a series of protocols as described below.

Soluble selections were performed essentially as described in Hawkins et al. (1992. J Mol. Bio. 226:889-896) with naïve human phage display libraries cloned into a phagemid vector, based on the filamentous phage M13 (Lloyd et al., 2009, Protein Eng. Des. Sel, 22:159-168; Vaughan et al., 1996, Nat. Biotechnol, 14:309-314). Anti-PrP$^c$ antibodies were isolated using an alternating series of selections against biotinylated human and cynomolgus PrP$^c$ 23-111 (AX436 or AX437). Essentially, libraries were blocked with 3% Marvel in PBS for 1 hour before the addition of biotinylated human (rounds 1 and 3) or cynomolgus PrP$^c$ 23-111 (round 2) to a final concentration of 100 nM. This was incubated for 1 hour at room temperature, and then single-chain variable fragments (scFv)-phage bound antigen was removed using streptavidin-coated paramagnetic beads (Dynabeads®, M-280) following manufacturer's recommendations. Bead/scFv-phage/antigen complexes were washed five times using PBS/Tween (0.1% v/v) to remove unbound scFv-phage and bound phage particles were eluted with Trypsin at 37° C. for 30 minutes. The eluate was used to infect log phase E. coli TG1 bacteria. Binders were rescued with the addition of M13 K07 helper phage, to generate scFv-phage particles for the next round of selection. Three rounds of selection were performed, and output was sequenced and tested for specificity after rounds 2 and 3 by phage ELISA. Crude periplasmic scFv were tested in Homogenous Time Resolved Fluorescence (HTRF) binding assays. Clones were picked based on sequence diversity and the periplasmic binding data, for expression and purification on nickel agarose. Purified scFvs were retested for binding and confirmed clones selected for reformatting as human IgG1-TM.

Three (non-Vernier) framework amino acid residues in clone PrP$^c$0123 variable light (VL) chain were reverted back to the closest human germline VL sequence IGLV1-47*02. Primers were designed to mutate the designated residues within the scFv sequence (within the pCANTAB6 vector) using the Quik change lightning multisite-directed mutagenesis kit (Agilent cat #210514) as directed in the product manual. The following amino acid residues were mutated: Kabat residue 20 from Thr to Ala, Kabat residue 38 from his to Gln, and Kabat residue 74 from Val to Ala (Kabat numbering system as described in Kabat and Wu, 1991). DNA was sequenced using pCANTAB6 vector sequence specific primers. There were no non-Vernier, framework differences between the closest variable heavy (VH) human germline sequence (IGHV3-23*01) and clone PrP$^c$-0123 VH and therefore no mutagenesis was required.

ScFv clones were converted to null effector function IgG$_1$-TM whole immunoglobulin by sub cloning into human VH and VL vectors as described in Douthwaite et al, 2015, Mabs, 7(1):152-166. Vectors were transiently transfected into a CHO mammalian expression system (fully described in Daramola et al., 2014, Biotechnol Prog., 30(1):132-41) for IgG expression. Culture supernatants were harvested and purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al., 1992). The purified IgG were analyzed for aggregation and degradation purity using SEC-HPLC and by SDS-PAGE.

PrP$^c$-0123 was affinity matured in vitro using a targeted CDR mutagenesis approach. A number of phage scFv libraries were constructed using oligonucleotide-directed mutagenesis and standard molecular biology techniques each targeting 6 residues for randomization across VH CDR 1, 2, 3 and VL CDR3 (as described in Clarkson T. and Lowman H., 2004). These libraries were used as the basis for further phage display affinity-based soluble selections using biotinylated human PrP$^c$ 23-111 (FC146). These selections differed from those described previously in that, concentrations of biotinylated PrP$^c$ 23-111 were reduced in successive rounds to increase the stringency of the selections. After each round, a number of representative clones were isolated, sequenced and then screened as soluble scFv fragments in a periplasmic HTRF assay for their ability to compete for binding to PrP$^c$ 23-111 against the parental clone PrP$^c$-0123 (epitope competition assay). Clones with the best inhibition values were expressed and re-confirmed in the HTRF competition assay as purified scFvs before being reformatted onto human IgG1-TM backbone (as described previously). Purified IgGs were ranked by IC50 informing the decision to recombine the most potent VH sequences obtained from the VH CDR3 mutagenesis libraries, with a single improved VL sequence obtained from the VL mutagenesis libraries. The reformatted VH and VL plasmids for these combinations were co-transfected for expression and purification as IgG. The combination of a particular VH clone and a VL clone formed a new clone referred to herein as "PrP$^c$-O0059", wherein the PrP$^c$-O0059 comprised the amino acid sequence SEQ ID NO: 4 and SEQ ID NO: 13. Characterization of PrP$^c$-O0059 is discussed in Examples 2, 3 and 4 below.

Example 2

Potency of the PrP$^c$-O0059

The potency of PrP$^c$-O0059 was determined in an epitope competition assay using directly labeled anti-CD230 (Prion) antibody 6D11 Mu IgG$_{2a}$ (BioLegend, San Diego, Calif.).

PrP$^c$-O0059 Hu IgG$_1$ was tested for its ability to inhibit directly labeled 6D11 binding to the recombinant N-terminal fragment of cellular prion protein (23-111 amino-acids) human PrP$^c$_N1, using HTRF in an epitope competition format.

Briefly, an HTRF assay was developed whereby a FRET signal was seen when DyLight 650-labelled 6D11 bound to human PrP$^c$_N1 complexed with an anti-FLAG europium cryptate labelled antibody. 6D11 was labeled with dylight650 according to the manufactures instructions (DyLight™ 650 Microscale Antibody Labeling Kit, ThermoFisher Scientific).

Final assay conditions were as follows: A serial dilution of PrP$^c$-O0059, Anti-FLAG Europium cryptate (CisBio) (100 pM), FLAG-tagged human PrP$^c$_N1 (300 pM) and DyLight650-labeled 6D11 (10 nM) were added to a black shallow-384-well plate (Costar), sealed, covered and incubated at room temperature for 4 hours. Plates were then read using an Envision microplate reader (PerkinElmer) using a 320 nm excitation filter and 590 nm & 665 nm emission filters. Ratios for the emission values seen at 665 nm & 620 nm were calculated using the following formula, (665/620) *10,000. Finally DeltaF values were calculated using the following formula, ((Test well ratio−non-specific background ratio)/non-specific background ratio)*100. Non-specific background was defined as the HRTF signal seen in control wells (typically wells I23 to P24 inclusive) where the addition of FLAG-tagged human PrP$^c$_N1 was omitted and replaced with assay buffer.

In order to determine the potency of PrP$^c$-O0059 compared to 6D11 at inhibiting the interaction of human PrP$^c$_N1 and Dylight650-labelled 6D11, 11-point dose response experiments were performed with concentrations of test IgG in duplicate. These titrations were added to the above HTRF competition assay and the data fitted to a Sigmoidal dose response model (variable slope) Y=Bottom+ (Top−Bottom)/(1+10^((Log EC50−X)*HillSlope)) where; X is the logarithm of concentration. Y is the response; Y starts at Bottom and goes to Top with a sigmoid shape. This was the "four parameter logistic equation". Data analysis was performed using Microsoft Excel and GraphPad Prism software.

As illustrated in FIG. 1, the results of these experiments showed a significant improvement in the geometric mean potency of PrP$^c$-O0059 over unlabeled 6D11 (Geomean IC50 of the PrP$^c$-O0059:2.247e-10 M [CI 1.29e-10 to 3.912e-10] n=6 & 6D11: 1.755e-08 M [CI 7.510e-09 to 4.099e-08] n=4).

Example 3

Direct HTRF Binding to Determine Species Cross-Reactivity

The ability of PrP$^c$-O0059 IgG$_1$ to bind to PrP$^c$-N1 derived from different species was determined by an HTRF biochemical binding assay.

Briefly, an HTRF assay was developed to determine if the test antibody bound to PrP$^c$_N1 derived from Human, Mouse, Rat or Cynomolgus Monkey. Detection of binding was performed by the FRET signal generated upon an anti-Human Fc IgG conjugated to XL665 binding to the test IgG and anti-FLAG europium cryptate-labeled antibody pre-complexed with PrP$^c$_N1 via an N-terminal FLAG tag.

Final assay conditions were as follows: A serial dilution of PrP$^c$-O0059, Anti-FLAG Europium cryptate (CisBio) (1 nM), FLAG-tagged human, Mouse, Rat or Cynomolgus PrP$^c$_N1 (5 nM) and anti-Human FcIgG labeled with XL665 (CisBio) (15 nM) were added to a black shallow-384-well plate(Costar), sealed, covered and incubated at room temperature for 4 hours. Plates were then read using an Envision microplate reader (PerkinElmer) using a 320 nm excitation filter and 590 nm and 665 nm emission filters. Ratios for the emission values seen at 665 nm and 620 nm were calculated using the following formula, (665/620)*10,000. Finally DeltaF values were calculated using the following formula, ((Test well ratio−non-specific background ratio)/non-specific background ratio)*100. Non-specific background was defined as the HRTF signal seen in control wells (typically wells I23 to P24 inclusive) where the addition of FLAG-tagged human PrP$^c$_N1 was omitted and replaced with assay buffer.

Eleven-point dose response experiments were performed with concentrations of test IgG in duplicate. These titrations were added to the above HTRF competition assay and the data analysis was performed using Microsoft Excel and GraphPad Prism software.

Figure 2:
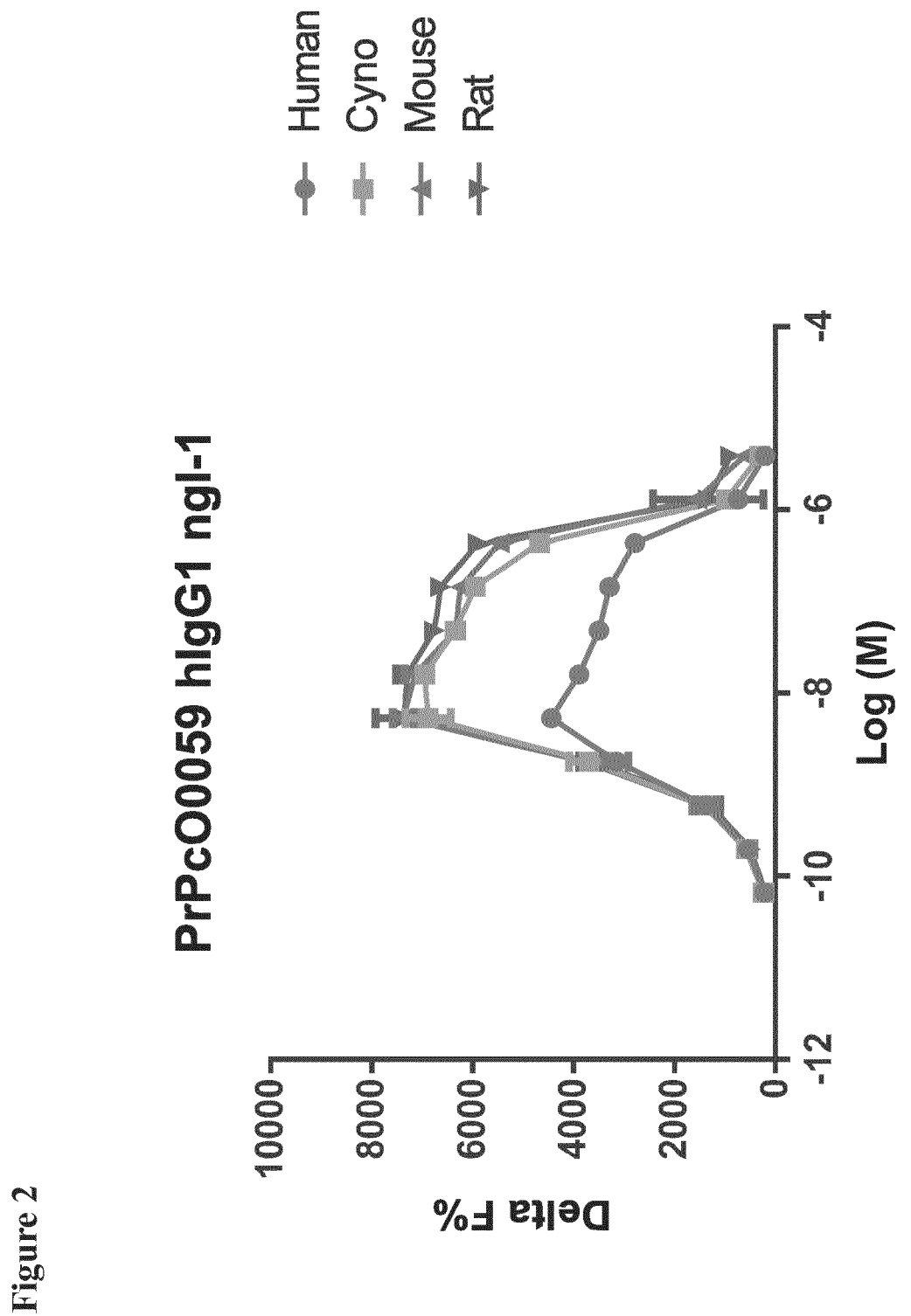
FIG. 2 shows the mean % Delta-F for PrP$^C$-O0059 hIgG1 binding to PrP$^c$_N1. Ngl-1 is non-germlined.
Figure 3:
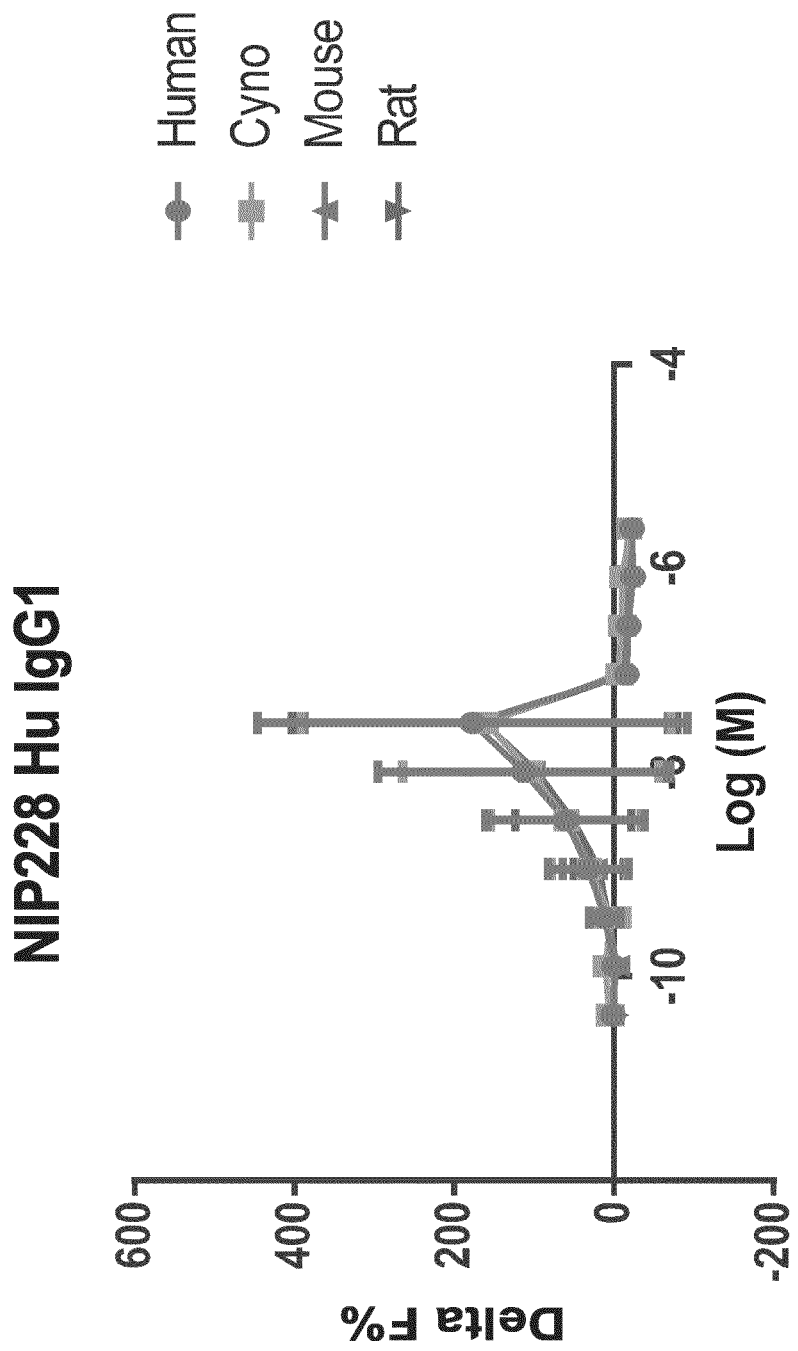
FIG. 3 shows the mean % Delta-F for the Isotype Control (NIP228) hIgG1 binding to PrP$^c$_N1.

The results of these experiments show that (Test Anti-PrP Ab) IgG$_1$ binds to PrP$^c$_N1 derived from Human, Rat, Mouse & Cynomolgus Monkey (FIG. 2). NIP228 Human IgG1 isotype control showed little or no binding to PrP$^c$_N1 (see FIG. 3).

Example 4

Binding Properties of the PrP$^c$-O0059 Antibody

Binding properties of PrP$^c$-O0059, 6D11 and Saf32 were determined by flow cytometry for human and cynomolgus cell lines. PrP$^c$-O0059HuIgG1 was tested for its ability to bind to full length PrP$^c$ present on cell lines of human, mouse and cynomolgus origin by flow cytometry.

Briefly, cells (approx 80% confluent) were harvested and centrifuged for 5 minutes at 1200 rpm before being re-suspended in PBS, counted and PBS added to adjust cell density to 1e6/mL. Two hundred microliters of cell suspension were added to wells of a 96 well plate and the plate spun at 1200 rpm to collect the cells. Pellets were re-suspended in 50 µl FACS buffer (1% BSA v/v in PBS) containing the appropriate antibody at 5 µg/ml followed by gentle mixing before being incubated on ice for 1 hour. Cells were then washed with buffer and secondary detection anti-mouse PE-conjugated F(ab')2 or anti-human-Fc PE-conjugated IgG at 5 µg/ml added to each well and incubated on ice for 1 hour before being washed 3 times as described above. Cell fix was diluted to 10% final in PBS and 50 µl added to each well for 10 mins followed by addition of 150 µl of FACS buffer to each well and the plate sealed and stored at 4° C. before being analyzed using an Intellicyte HTFC system.

PrP$^c$-O0059 Hu IgG1 and the positive controls 6D11 and Saf-32 were shown to bind to both the human CCRF-CEM and cynomolgus CynoMK-1 cell lines, while 6D11 did not show any binding above background to the CynoMK-1 cell line.

The affinity of the anti-PrP$^c$ antibody PrPc0059, was determined using the ProteOn XPR36 (Bio-Rad) biosensor. Protein G was amine-coupled to the GLC chip at a concentration of 10 µg/ml in 10 mM sodium acetate buffer, pH 3.65. Antibody PrPc0059 was diluted to 1 µg/ml in HBS-EP+ and flowed over the Protein G coupled chip surface at 30 µl/min. Human PrP$^c$_N1_Flag His protein was serially diluted from 250 nM to 15.6 nM and flowed over the chip at 30 µl/min, allowing 2 minutes for association and 18 minutes for dissociation. The chip temperature was maintained at 35° C. The data is fitted to a 1:1 model. The antibody was determined to have a $K_D$ of 23.5 pM, $k_a$ of $5.64 \times 10^5$ M$^{-1}$ s$^{-1}$ and a $k_d$ value of $1.33 \times 10^{-5}$ s$^{-1}$.

SEQUENCE LISTING:

SEQ ID NO: 1: Human Prion Protein Amino Acid
Sequence (GenBank Accession No. NP_001073592.1)
MANLGCWMLVLFVATWSDLGLCKKRPKPGGWNTGGSRYPGQGSPGGNRYP
PQGGGGWGQPHGGGWGQPHGGGWGQPHGGGWGQPHGGGWGQGGGTHSQWN
KPSKPKTNMKHMAGAAAAGAVVGGLGGYMLGSAMSRPIIHFGSDYEDRYY
RENMHRYPNQVYYRPMDEYSNQNNFVHDCVNITIKQHTVTTTTKGENFTE
TDVKMMERVVEQMCITQYERESQAYYQRGSSMVLFSSPPVILLISFLIFL
IVG SEQ ID NO: 2: Cynomolgus Monkey Prion Protein
Amino Acid Sequence
MANLGCWMLVLFVATWSDLGLCKKRPKPGGWNTGGSRYPGQGSPGGNRYP
PQGGGGWGQPHGGGWGQPHGGGWGQPHGGGWGQPHGGGWGQGGGTHNQWH
KPSKPKTSMKHMAGAAAAGAVVGGLGGYMLGSAMSRPLIHFGNDYEDRYY
RENMYRYPNQVYYRPVDQYSNQNNFVHDCVNITIKQHTVTTTTKGENFTE
TDVKMMERVVEQMCITQYEKESQAYYQRGSSMVLFSSPPVILLISFLIFL
IVG SEQ ID NO: 3: Nucleic Acid Sequence Encoding VH of
Representative Anti-PrP$^C$ Antibody or Antigen-
Binding Fragment
gaggtgcagctgttggagtctgggggaggcttggtacagcctgggggtc
cctgagactctcctgtgcagcctctggattcacctttagcagctatgcca
tgagctgggtccgccaggctccagggaaggggctggagtgggtctcagct
attagtggtagtggtggtagcacatactacgcagactccgtgaagggccg
gttcaccatctccagagacaattccaagaacacgctgtatctgcaaatga
acagcctgagagccgaggacacgccgtgtattactgtgcgaaagtgatg
gaggagctccagaacaactttgcctactggggccaagggacaatggtcac
cgtctcctca SEQ ID NO: 4: Amino Acid Sequence Encoding VH of
Representative Anti-PrP$^C$ Antibody or Antigen-
Binding Fragment
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKVM
EELQNNFAYWGQGTMVTVSS SEQ ID NO: 5: VH CDR1 Amino Acid Sequence for
Representative Anti-PrP$^C$ Antibody or Antigen-
Binding Fragment
SYAMS SEQ ID NO: 6: VH CDR2 Amino Acid Sequence for
Representative Anti-PrP$^C$ Antibody or Antigen-
Binding Fragment
AISGSGGSTYYADSVKG SEQ ID NO: 7: VH CDR3 Amino Acid Sequence for
Representative Anti-PrP$^C$ Antibody or Antigen-
Binding Fragment
VMEELQNNFAY

SEQUENCE LISTING:

SEQ ID NO: 8: VH Framework 1 Amino Acid Sequence for Representative Anti-PrP$^C$ Antibody or Antigen-Binding Fragment
EVQLLESGGGLVQPGGSLRLSCAASGFTFS SEQ ID NO: 9: VH Framework 2 Amino Acid Sequence for Representative Anti-$PrP^C$ Antibody or Antigen-Binding Fragment
WVRQAPGKGLEWVS SEQ ID NO: 10: VH Framework 3 Amino Acid Sequence for Representative Anti-$PrP^C$ Antibody or Antigen-Binding Fragment
RFTISRDNSKNTLYLQMNSLRAEDTAVYYCAK SEQ ID NO: 11: VH Framework 4 Amino Acid Sequence for Representative Anti-$PrP^C$ Antibody or Antigen-Binding Fragment
WGQGTMVTVSS SEQ ID NO: 12: Nucleic Acid Sequence Encoding VL of Representative Anti-$PrP^C$ Antibody or Antigen-Binding Fragment
cagtctgtgctgactcagccaccctcggcgtctgggacccccgggcagag
ggtcaccatctcctgttctggagaaaggtccgacatcggaattaattatg
tctcctggtaccaacagctgccaggaacggcccccaaactgctcatctac
acagatgaccggaggcccccgggagtccctgaccgattctctgcctccaa
gtctggcacctcagcctccctggccatcagtgggctccggtccgaggatg
aggctgattattattgtgaggcgtggcatgacgtgttggggcacccggtc
ttcggcggagggaccaagctgaccgtccta SEQ ID NO: 13: Amino Acid Sequence Encoding VL of Representative Anti-$PrP^C$ Antibody or Antigen-Binding Fragment
QSVLTQPPSASGTPGQRVTISCSGERSDIGINYVSWYQQLPGTAPKLLIY
TDDRRPPGVP
DRFSASKSGTSASLAISGLRSEDEADYYCEAWHDVLGHPVFGGGTKLTVL SEQ ID NO: 14: VL CDR1 Amino Acid Sequence for Representative Anti-$PrP^C$ Antibody or Antigen-Binding Fragment
SGERSDIGINYVS SEQ ID NO: 15: VL CDR2 Amino Acid Sequence for Representative Anti-$PrP^C$ Antibody or Antigen-Binding Fragment
TDDRRPP -continued

SEQUENCE LISTING:

SEQ ID NO: 16: VL CDR3 Amino Acid Sequence for Representative Anti-$PrP^C$ Antibody or Antigen-Binding Fragment
EAWHDVLGHPV SEQ ID NO: 17: VL Framework 1 Amino Acid Sequence for Representative Anti-$PrP^C$ Antibody or Antigen-Binding Fragment
QSVLTQPPSASGTPGQRVTISC SEQ ID NO: 18: VL Framework 2 Amino Acid Sequence for Representative Anti-$PrP^C$ Antibody or Antigen-Binding Fragment
WYQQLPGTAPKLLIY SEQ ID NO: 19: VL Framework 3 Amino Acid Sequence for Representative Anti-$PrP^C$ Antibody or Antigen-Binding Fragment
GVPDRFSASKSGTSASLAISGLRSEDEADYYC SEQ ID NO: 20: VL Framework 4 Amino Acid Sequence for Representative Anti-$PrP^C$ Antibody or Antigen-Binding Fragment
FGGGTKLTVL SEQ ID NO: 21: Rat Prion Protein Amino Acid Sequence
MANLGYWLLALFVTTCTDVGLCKKRPKPGGWNTGGSRYPGQGSPGGNRYP
PQSGGTWGQPHGGGWGQPHGGGWGQPHGGGWGQPHGGGWSQGGGTHNQWN
KPSKPKTNLKHVAGAAAAGAVVGGLGGYMLGSAMSRPMLHFGNDWEDRYY
RENMYRYPNQVYYRPVDQYSNQNNFVHDCVNITIKQHTVTTTTKGENFTE
TDVKMMERVVEQMCVTQYQKESQAYYDGRRSSAVLFSSPPVILLISFLIF
LIVG

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An antibody or antigen-binding fragment, wherein the antibody or antigen-binding fragment comprises a VH CDR1 having the amino acid sequence of SEQ ID NO: 5, a VH CDR2 having the amino acid sequence of SEQ ID NO: 6, and a VH CDR3 having the amino acid sequence of SEQ ID NO: 7, and comprises a VL CDR1 having the amino acid sequence of SEQ ID NO: 14, a VL CDR2 having the amino acid sequence of SEQ ID NO: 15, and a VL CDR3 having the amino acid sequence of SEQ ID NO: 16.

2. The antibody or antigen-binding fragment of claim 1, wherein the antibody or antigen-binding fragment comprises a light chain variable (VL) domain and a heavy chain variable (VH) domain; wherein the VL domain comprises CDR1, CDR2 and CDR3 of the amino acid sequence set forth in SEQ ID NO: 13.

3. The antibody or antigen-binding fragment of claim 1, wherein the antibody or antigen-binding fragment comprises a light chain variable (VL) domain and a heavy chain variable (VH) domain; wherein the VH domain comprises CDR1, CDR2 and CDR3 of the amino acid sequence set forth in SEQ ID NO: 4.

4. The antibody or antigen-binding fragment of claim 1, wherein the VH domain comprises framework regions that are at least 90% identical to the amino acid sequences of one or more of SEQ ID NO: 8, SEQ ID NO: 9, SEQ ID NO: 10 and SEQ ID NO: 11.

5. The antibody or antigen-binding fragment of claim 1, wherein the VL domain comprises framework regions that are at least 90% identical to the amino acid sequences of one or more of SEQ ID NO: 17, SEQ ID NO: 18, SEQ ID NO: 19 and SEQ ID NO: 20.

6. The antibody or antigen-binding fragment of claim 1, wherein the VH domain comprises an amino acid sequence that is at least 90% identical to SEQ ID NO: 4 and/or the VL domain comprises an amino acid sequence that is at least 90% identical to SEQ ID NO: 13.

7. The antibody or antigen-binding fragment of claim 1, wherein the antibody or antigen-binding fragment is humanized or human.

8. The antibody or antigen-binding fragment of claim 1, wherein the antibody or antigen-binding fragment is encoded by a nucleic acid comprising a nucleotide sequence that is at least 90% identical to SEQ ID NO: 3 or a nucleotide sequence that is at least 90% identical to SEQ ID NO: 12.

9. The antibody or antigen-binding fragment of claim 1, wherein the antibody or antigen-binding fragment competes with 6D11 antibody for binding to $PrP^c$.

10. The antibody or antigen-binding fragment of claim 1, wherein the antibody or antigen-binding fragment binds to one or more of human, rat, mouse, or cynomolgus monkey $PrP^c$.

11. A composition comprising a pharmaceutically acceptable carrier and the antibody or antigen-binding fragment of claim 1.

12. A kit comprising the antibody or antigen-binding fragment of claim 1.

* * * * *

SEQUENCE LISTING

<160> NUMBER OF SEQ ID NOS: 21

<210> SEQ ID NO 1
<211> LENGTH: 253
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
    50                  55                  60

```
Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 2
<211> LENGTH: 253
<212> TYPE: PRT
<213> ORGANISM: Macaca fascicularis

<400> SEQUENCE: 2

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
 50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Asn Gln Trp His Lys Pro Ser Lys Pro Lys Thr Ser Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Leu Ile His Phe Gly Asn Asp
    130                 135                 140

Tyr Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190
```

Thr Lys Gly Glu Asn Phe Thr Glu Thr Asp Val Lys Met Met Glu Arg
            195                 200                 205

Val Val Glu Gln Met Cys Ile Thr Gln Tyr Glu Lys Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
            245                 250

<210> SEQ ID NO 3
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaagtgatg     300
gaggagctcc agaacaactt tgcctactgg ggccaaggga caatggtcac cgtctcctca     360

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Glu Glu Leu Gln Asn Asn Phe Ala Tyr Trp Gly Gln
            100                 105                 110

Gly Thr Met Val Thr Val Ser Ser
        115                 120

<210> SEQ ID NO 5
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 5

Ser Tyr Ala Met Ser
1               5

<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Ile Ser Gly Ser Gly Gly Ser Thr Tyr Tyr Ala Asp Ser Val Lys
1               5                   10                  15

Gly

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Val Met Glu Glu Leu Gln Asn Asn Phe Ala Tyr
1               5                   10

<210> SEQ ID NO 8
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Trp Val Arg Gln Ala Pro Gly Lys Gly Leu Glu Trp Val Ser
1               5                   10

<210> SEQ ID NO 10
<211> LENGTH: 32
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 10

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Gly Gln Gly Thr Met Val Thr Val Ser Ser
1               5                   10

<210> SEQ ID NO 12
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
cagtctgtgc tgactcagcc accctcggcg tctgggaccc ccgggcagag ggtcaccatc     60
tcctgttctg gagaaaggtc cgacatcgga attaattatg tctcctggta ccaacagctg    120
ccaggaacgg cccccaaact gctcatctac acagatgacc ggaggccccc gggagtccct    180
gaccgattct ctgcctccaa gtctggcacc tcagcctccc tggccatcag tgggctccgg    240
tccgaggatg aggctgatta ttattgtgag gcgtggcatg acgtgttggg cacccggtc     300 ttcggcggag ggaccaagct gaccgtccta                                      330

<210> SEQ ID NO 13
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Ser Gly Glu Arg Ser Asp Ile Gly Ile Asn
                20                  25                  30

Tyr Val Ser Trp Tyr Gln Gln Leu Pro Gly Thr Ala Pro Lys Leu Leu
            35                  40                  45

Ile Tyr Thr Asp Asp Arg Arg Pro Gly Val Pro Asp Arg Phe Ser
        50                  55                  60

Ala Ser Lys Ser Gly Thr Ser Ala Ser Leu Ala Ile Ser Gly Leu Arg
65                  70                  75                  80

```
Ser Glu Asp Glu Ala Asp Tyr Tyr Cys Glu Ala Trp His Asp Val Leu
                85                  90                  95
Gly His Pro Val Phe Gly Gly Gly Thr Lys Leu Thr Val Leu
            100                 105                 110

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic
      peptide"

<400> SEQUENCE: 14

Ser Gly Glu Arg Ser Asp Ile Gly Ile Asn Tyr Val Ser
1               5                   10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Thr Asp Asp Arg Arg Pro Pro
1               5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Ala Trp His Asp Val Leu Gly His Pro Val
1               5                   10

<210> SEQ ID NO 17
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 18

Trp Tyr Gln Gln Leu Pro Gly Thr Ala Pro Lys Leu Leu Ile Tyr
1               5                   10                  15

<210> SEQ ID NO 19
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gly Val Pro Asp Arg Phe Ser Ala Ser Lys Ser Gly Thr Ser Ala Ser
1               5                   10                  15

Leu Ala Ile Ser Gly Leu Arg Ser Glu Asp Glu Ala Asp Tyr Tyr Cys
                20                  25                  30

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Phe Gly Gly Gly Thr Lys Leu Thr Val Leu
1               5                   10

<210> SEQ ID NO 21
<211> LENGTH: 254
<212> TYPE: PRT
<213> ORGANISM: Rattus sp.

<400> SEQUENCE: 21

Met Ala Asn Leu Gly Tyr Trp Leu Leu Ala Leu Phe Val Thr Thr Cys
1               5                   10                  15

Thr Asp Val Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Ser Gly Gly Thr Trp Gly Gln Pro His Gly Gly Gly
        50                  55                  60

Trp Gly Gln Pro His Gly Gly Trp Gly Gln Pro His Gly Gly Gly
65                  70                  75                  80

Trp Gly Gln Pro His Gly Gly Gly Trp Ser Gln Gly Gly Thr His
                85                  90                  95

Asn Gln Trp Asn Lys Pro Ser Lys Pro Lys Thr Asn Leu Lys His Val
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Met Leu His Phe Gly Asn Asp
        130                 135                 140

Trp Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

-continued

```
His Asp Cys Val Asn Ile Thr Ile Lys Gln His Thr Val Thr Thr Thr
            180             185             190

Thr Lys Gly Glu Asn Phe Thr Glu Thr Asp Val Lys Met Met Glu Arg
        195             200             205

Val Val Glu Gln Met Cys Val Thr Gln Tyr Gln Lys Glu Ser Gln Ala
    210             215             220

Tyr Tyr Asp Gly Arg Arg Ser Ser Ala Val Leu Phe Ser Ser Pro Pro
225             230             235             240

Val Ile Leu Leu Ile Ser Phe Leu Ile Phe Leu Ile Val Gly
            245             250
```